(12) United States Patent
Gendron et al.

(10) Patent No.: US 7,640,171 B2
(45) Date of Patent: Dec. 29, 2009

(54) ASSET COMMUNICATION FORMAT WITHIN A COMPUTER NETWORK

(75) Inventors: David Pierre Gendron, Coon Rapids, MN (US); Dale Philip Kingsbury, Little Canada, MN (US); Jeffrey Allen Romatoski, Woodbury, MN (US); Larry Robert Sitka, Stillwater, MN (US)

(73) Assignee: Acuo Technologies, LLC, Oakdale, MN (US)

( * ) Notice: Subject to any disclaimer, the term of this patent is extended or adjusted under 35 U.S.C. 154(b) by 1974 days.

(21) Appl. No.: 09/911,846

(22) Filed: Jul. 24, 2001

(65) Prior Publication Data

US 2002/0028007 A1    Mar. 7, 2002

Related U.S. Application Data

(60) Provisional application No. 60/220,586, filed on Jul. 25, 2000.

(51) Int. Cl.
*G06Q 50/00* (2006.01)
*G06K 9/00* (2006.01)
*G06F 15/173* (2006.01)

(52) U.S. Cl. ............................. 705/2; 382/128; 709/238
(58) Field of Classification Search .................. None
See application file for complete search history.

(56) References Cited

U.S. PATENT DOCUMENTS

| | | | |
|---|---|---|---|
| 4,847,694 A | 7/1989 | Nishihara et al. | |
| 5,469,353 A | 11/1995 | Pinsky et al. | 382/131 |
| 5,513,101 A | 4/1996 | Pinsky et al. | 705/3 |
| 5,517,405 A | 5/1996 | McAndrew et al. | 706/45 |
| 5,642,513 A * | 6/1997 | Schnellinger et al. | 717/141 |
| 5,654,555 A | 8/1997 | Buytaert et al. | 250/581 |
| 5,655,084 A | 8/1997 | Pinsky et al. | 705/3 |
| 5,671,353 A | 9/1997 | Tian et al. | 714/48 |
| 5,881,225 A | 3/1999 | Worth | 713/200 |
| 5,883,985 A * | 3/1999 | Pourjavid | 382/274 |

(Continued)

FOREIGN PATENT DOCUMENTS

WO    WO 99/01859    1/1999

OTHER PUBLICATIONS

"Processing Structure For Real Time Processing Of Medical Ultra-Sound Images", Lokberg, Ola, 1992, Computer Science, vol. 54/02-C Of Dissertation Abstracts International, p. 589, Dialog File 35, Acc. No. 01285388.*

(Continued)

*Primary Examiner*—C. Luke Gilligan
*Assistant Examiner*—Rachel L Porter
(74) *Attorney, Agent, or Firm*—Brooks, Cameron & Huebsch, PLLC

(57) ABSTRACT

A communication format and protocol is described for routing and storage "asset" within a computer network. The assets conform to a format in which a first data structure that stores asset meta information to control routing of the asset through a medical imaging network. A second data structure that stores medical imaging information received from a medical imaging modality. A third data structure that stores pixel data received from the medical imaging modality. A fourth data structure that stores patch data that includes modifications to the medical imaging information. A fifth data structure that stores error detection and correction information.

19 Claims, 20 Drawing Sheets

U.S. PATENT DOCUMENTS

| | | | |
|---|---|---|---|
| 5,886,693 A | 3/1999 | Ho et al. | 715/700 |
| 5,971,923 A * | 10/1999 | Finger | 600/437 |
| 5,987,345 A | 11/1999 | Engelmann et al. | 600/407 |
| 6,006,191 A | 12/1999 | DiRienzo | 705/2 |
| 6,032,120 A | 2/2000 | Rock et al. | 705/2 |
| 6,037,940 A | 3/2000 | Schroeder et al. | 715/763 |
| 6,065,073 A * | 5/2000 | Booth | 710/46 |
| 6,195,465 B1 * | 2/2001 | Zandi et al. | 382/248 |
| 6,282,441 B1 * | 8/2001 | Raymond et al. | 600/513 |
| 6,762,763 B1 * | 7/2004 | Migdal et al. | 345/506 |
| 6,820,057 B1 * | 11/2004 | Loch et al. | 705/2 |
| 2001/0013822 A1 * | 8/2001 | Nazarian et al. | 340/3.1 |
| 2002/0116509 A1 * | 8/2002 | DeLaHuerga | 709/229 |
| 2004/0039606 A1 * | 2/2004 | Loch et al. | 705/3 |

OTHER PUBLICATIONS

"Intelligent Image Management in a Distributed PACS and Telemedicine Environment" M. Tsiknakis et al., IEEE Communications Magazine, vol. 34(7), pp. 36-45, 1996.

* cited by examiner

```
08003000                              (0008,0030): Study Time. Decimal Tag: (0008,0048)
0c000000                              Tag Length: 12
3030303030302e3030303020              Tag Data: 000000.0000

08006000                              (0008,0060): Modality. Decimal Tag: (0008,0096)
02000000                              Tag Length: 2
4d52                                  Tag Data: MR 08007000                              (0008,0070): Manufacturer. Decimal Tag: (0008,0112)
18000000                              Tag Length: 24
5068696c697073204d65646963616c20      Tag Data: Philips Medical
53797374656d7320                      Tag Data: Systems 08008000                              (0008,0080): Institution Name. Decimal Tag: (0008,0128)
10000000                              Tag Length: 16
444f4149204d454d4f5249414c204850      Tag Data: DOAI MEMORIAL HP 08003010                              (0008,1030): Study Description. Decimal Tag: (0008,4144)
08000000                              Tag Length: 8
432d5350494e4520                      Tag Data: C-SPINE 10001000                              (0010,0010): Patient's Name. Decimal Tag: (0016,0016)
12000000                              Tag Length: 18
4d522f43205350494e452f5453452f32      Tag Data: MR/C SPINE/TSE/2
3536                                  Tag Data: 56

10003000                              (0010,0030): Patient's Birth Date. Decimal Tag: (0016,0048)
08000000                              Tag Length: 8
3139363430373331                      Tag Data: 19640731

10004000                              (0010,0040): Patient's Sex. Decimal Tag: (0016,0064)
02000000                              Tag Length: 2
4d20                                  Tag Data: M
```

FIG. 20

ASSET COMMUNICATION FORMAT WITHIN A COMPUTER NETWORK

This application claims priority from U.S. Provisional Application Ser. No. 60/220,586, filed Jul. 25, 2000, the entire content of which is incorporated herein by reference.

TECHNICAL FIELD

The invention relates to routing and storage within a computer network.

BACKGROUND

A computer network includes a variety of computing devices that communicate and share resources and data. A medical imaging environment, for example, may include a number of networked devices including a medical imaging modality that generates medical images of a patient, a diagnostic view station for displaying the images, an output device for printing the images on film or other media, and an archive system for storing the images. These devices are often collectively referred to as a Picture Archival and Retrieval System (PACS), and may communicate using a number of protocols. The American College of Radiology and National Electrical Manufacturers Association, for example, developed one such protocol referred to as Digital Imaging and Communications in Medicine (DICOM). In general, DICOM defines vendor-independent data formats and data transfer services for digital medical images.

In many conventional networks, the devices communicate over a packet-based network by dividing the data into small blocks called packets, which are individually routed across the network from a source device to a destination device. The destination device extracts the data from the packets and assembles the data into its original form. Dividing the data into packets enables the source device to resend only those individual packets that may be lost during transmission.

Certain devices, referred to as routers, maintain routing information that describes routes through the network. A "route" can generally be defined as a path between two locations on the network. Upon receiving an incoming packet, the router examines information within the packet to identify the destination for the packet. Based on the destination, the router forwards the packet in accordance with the routing information.

The routers often maintain the routing information, typically in the form of one or more routing tables. The form and contents of the routing tables often depends on the routing algorithm implemented by the router. Typically, networked medical imaging systems make use of general-purpose routers that perform the routing functions without knowledge of the particular medical images and associated patient data.

SUMMARY

In general, the invention is directed to a router that provides for seamless communication and distribution of medical images and other patient data between the medical modalities and other various medical imaging devices. As described in detail below, the router implements certain protocols and file formats to treat network communications as a self-describing "assets" that encapsulate medical imaging data. For example, a self-describing asset may include patient data, session data, study data, medical image data, private asset information, and the like. The assets conform to a format in which a first data structure that stores asset meta information to control routing of the asset through a medical imaging network. A second data structure that stores medical imaging information received from a medical imaging modality. A third data structure that stores pixel data received from the medical imaging modality. A fourth data structure that stores patch data that includes modifications to the medical imaging information. A fifth data structure that stores error detection and correction information.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 11-17 illustrates example user interfaces for reconciling errors within medical imaging data.

FIG. 20 illustrates an example display presented by such a tool for debugging and configuring a medical imaging environment.

DETAILED DESCRIPTION

Figure 1:
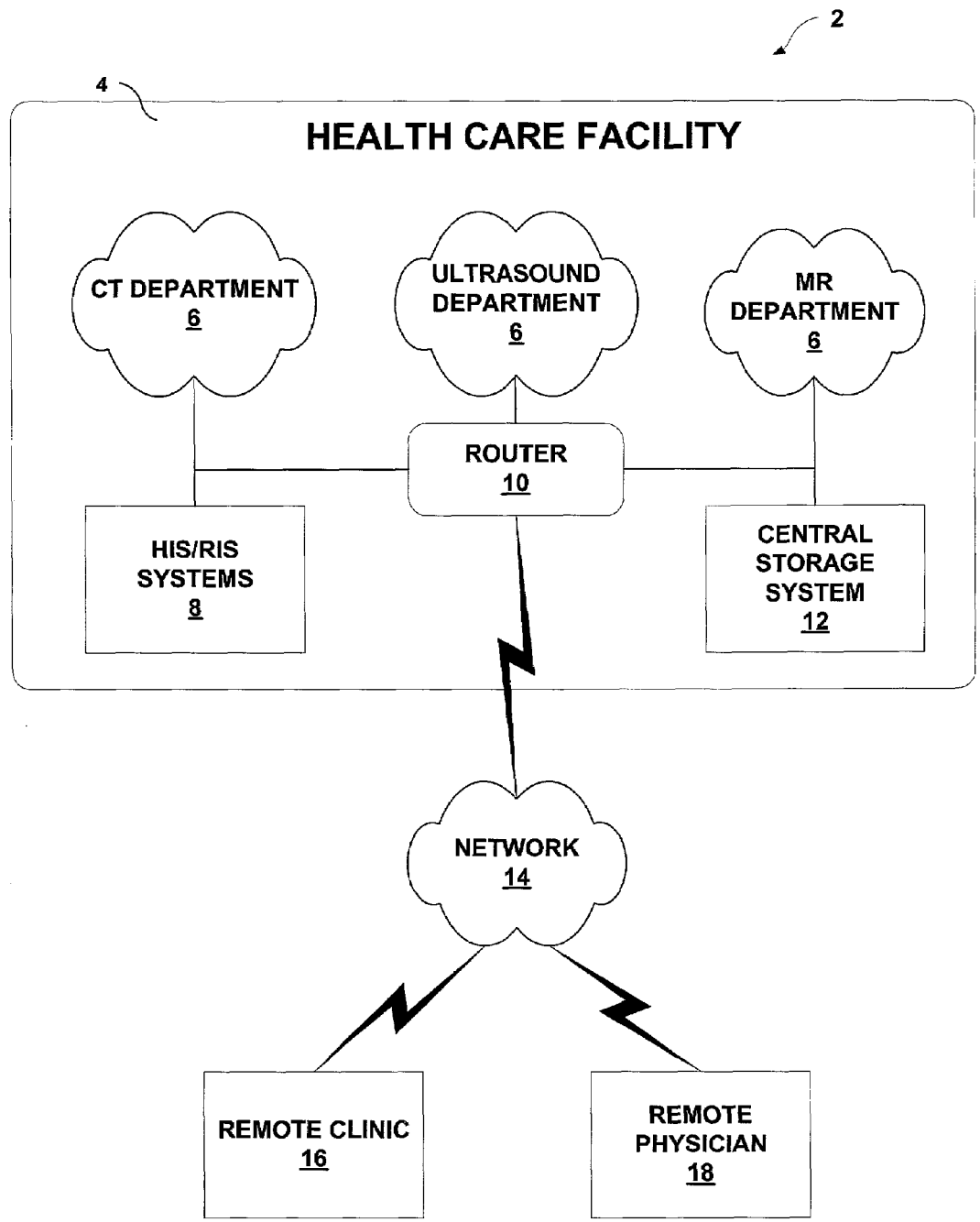
FIG. 1 is a block diagram illustrating an example system for communication and storage of medical imaging data in accordance with the principles of the invention.

FIG. 1 is a block diagram illustrating a system 2 for communication and storage of medical imaging data. In particular, system 2 includes a health care facility having a number of departments 6 interconnected by router 10. Each department 6 may include a number of medical imaging devices. Departments 6 may include, for example, medical modalities of different types, such as magnetic resonance (MR), computed tomography (CT), digital radiography (DR) or ultrasound. Each medical modality may have different imaging characteristics and features, and may generate substantially different patient data and associated medical images. Each department 6 may also include other medical imaging devices, such as a number of view stations for displaying and annotating medical images, an output device for printing the medical images, and a local archive for storing medical images.

In general, router 10 provides for seamless communication and distribution of medical images and other patient data between the medical modalities and other various medical imaging devices of departments 6. In particular, the medical modalities and other various medical imaging devices communicate medical imaging "assets" to router 10 for routing to other devices within system 2. As described in detail below, router 10 implements certain protocols and file formats to treat network communications as a self-describing "assets" that encapsulate medical imaging data. For example, a self-describing asset may include patient data, session data, study data, medical image data, private asset information, and the like.

Router 10 provides additional interfaces to other systems including a Hospital Information System/Radiology Information System (HIS/RIS) 8 that stores patient data, and a central storage system 12 that provides a central repository for the storage of medical assets. Router 10 also provides for remote communication of medical imaging assets over network 14 to remote clinic 16 and, for example, a remote physician 18 wishing to remotely view medical assets. Network 14 may be any Local Area Network (LAN) or Wide Area Network (WAN) or may be a global network such as the Internet.

Although illustrated within a medical imaging environment, many of the features and advantages of router 10 can be applied to a variety of environments, and to routing and data storage generally. For example, router 10 may be used in systems for managing assets generally, such as photographic assets, insurance information, billing and accounting information.

The medical imaging devices of system 2 communicate the assets over network 14 using a suitable network protocol. The medical modalities and other devices may, for example, exchange data and information using a data communications protocol developed by the American College of Radiology (ACR) and the National Electrical Manufacturers Association (NEMA) known as the Digital Imaging and Communications in Medicine (DICOM) protocol. Typically, the DICOM protocol may be implemented using TCP/IP connections between medical devices over a network, as illustrated in FIG. 1, or using a point-to-point communication medium.

As described in detail below, router 10 integrates routing, network management and storage functionality. Router 10, for example, receives assets and intelligently routes the assets to medical devices within system 2 in accordance with routing information. In addition, router 10 provides interfaces to storage systems by implementing, for example, a set of storage "classes" required by the DICOM protocol. In this manner, router 10 provides all functionality needed to seamlessly couple high-end imaging modalities and other medical devices directly to storage devices within a networked environment.

Figure 2:
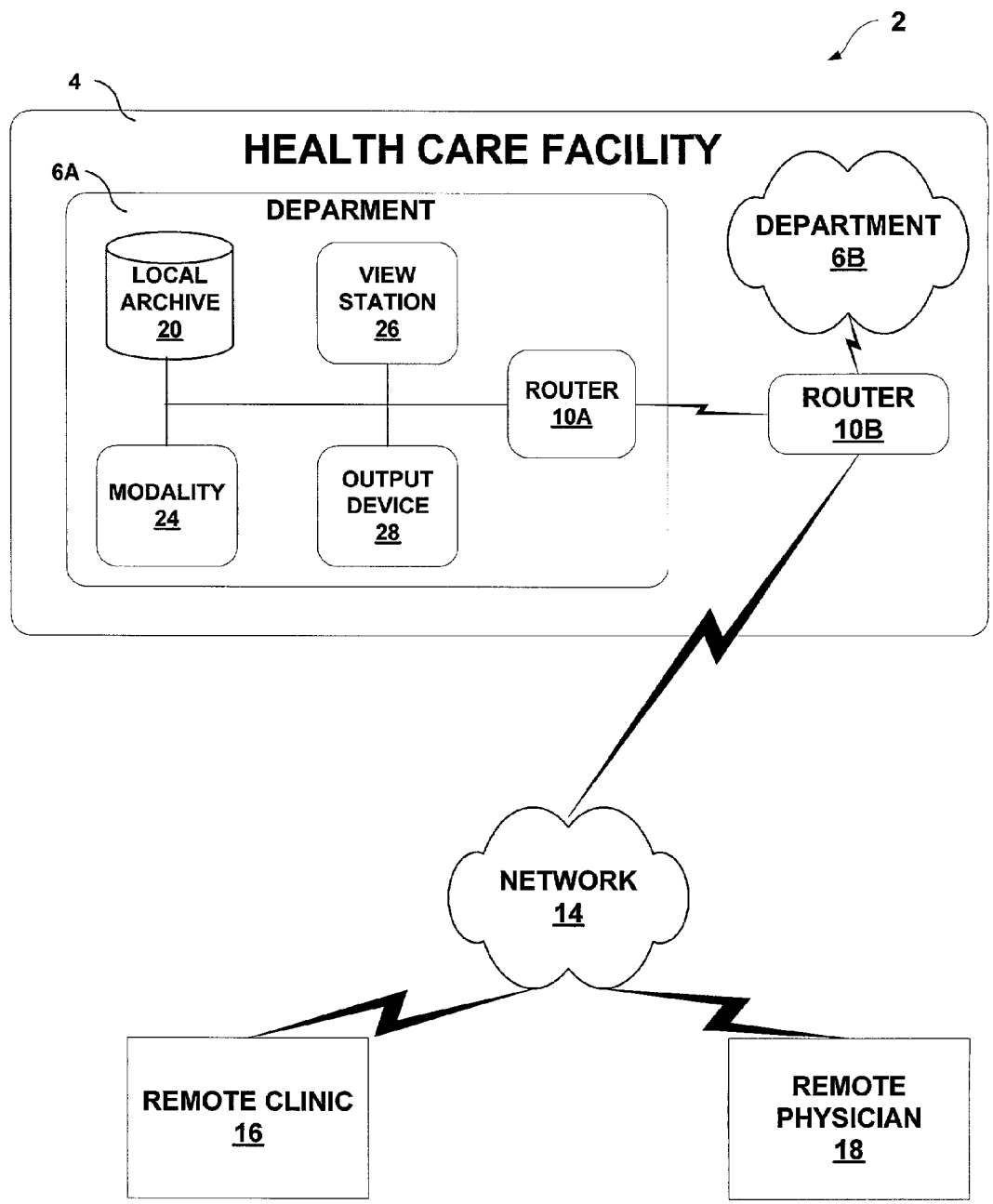
FIG. 2 is a block diagram illustrating an example department having a number of medical imaging devices coupled by routers.

FIG. 2 is a block diagram illustrating an example department 6A having a number of medical imaging devices coupled to network 14 by department router 10A and facility router 10B in accordance with the principles of the invention. Department router 10A routes images locally between, for example, medical modality 24, view station 26, local archive 20, and output device 28. Facility router 10B couples department 6A to department 6B and network 14, which may be a private or public network.

As illustrated, routers 10 integrate multiple medical imaging departments 6. Each department 6 may, for example, comprise a different DICOM "domain" having a set of DICOM Application Entities (AEs), each having an AE Title. In this manner, routers 10 allow medical professionals to perform collaborative studies on images, even when the professionals may be in different facilities, even across the country. More particularly, router 10A provides DICOM CFIND and CMOVE services to department 6A, and may be configured with a single AE for modality 24. In addition, router 10A may be configured to search for storage assets on local archive 20. Router 10B may be configured to forward CFIND and CMOVE requests to remote locations, including router 10A, remote clinic 16, remote physician 18 and one or more routers within department 6B.

In one embodiment, routers 10 manage the bandwidth consumed by medical imaging data as assets are routed between departments 6 and network 14. Medical imaging data is inherently large compared with other network communications, such as electronic mail (email), that may also be present within system 2. To minimize any negative impact on the other network communications, routers 10 controls and "throttles" medical imaging communications.

More specifically, to facilitate bandwidth management, routers 10 present user interfaces by which an operator can limit maximum bandwidth consumption for medical imaging network communications. The operator may indicate, for example, that such communications should consume no more than 60% of the available network bandwidth. As each of routers 10 output network communications, the routers 10 monitor the rates at which outbound data packets are transmitted, and insert sufficient time delays between transmissions to ensure the available bandwidth is reserved.

Furthermore, the operator may define additional information for a "link" within system 2. Generally, a link may be any physical connection between two devices in a network. The operator may define, for example, times at which the link is available, or cost per megabyte of data on the link. In addition, router 10 may automatically detect the bandwidth of links to adjacent nodes within system 2, typically by requesting such information from an operating system, such as Windows™ 2000, or one or more device drivers. Based on this information, routers 10 may select particular links and schedule network communications to minimize cost.

Figure 3:
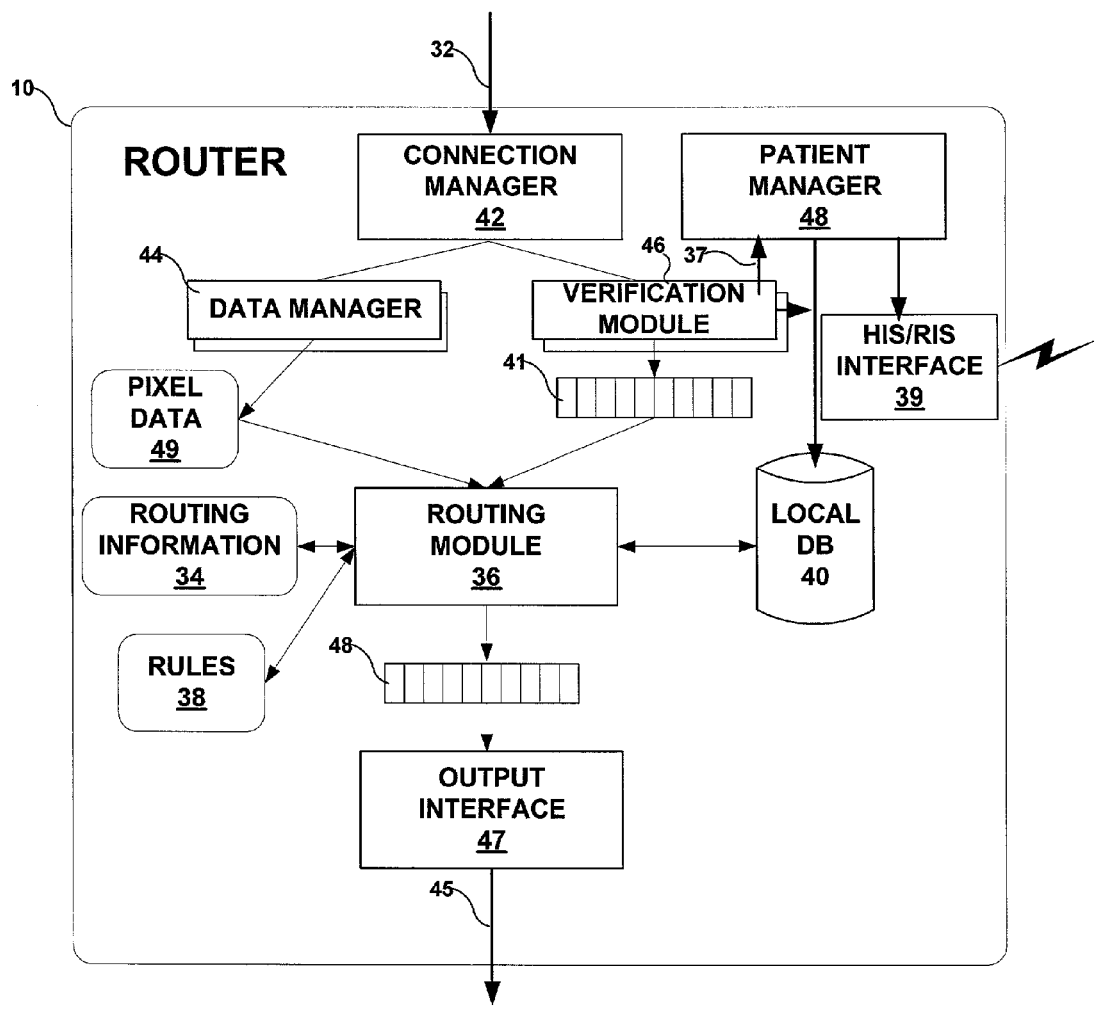
FIG. 3 is a block diagram illustrating an example embodiment of a router according to the principles of the invention.

FIG. 3 is a block diagram illustrating an example embodiment of router 10 according to the principles of the invention. In general, router 10 receives inbound network communication 32, often in the form of a storage asset communicated in one or more data packets, and forwards the network communication in accordance with routing information 34, which describes the topology of system 2. In particular, routing information 34 describes routes between the networked medical imaging devices within system 2. Although illustrated within a medical imaging environment for exemplary purposes, the techniques described herein are not so limited. Many of the features and advantages of router 10 can be applied to a variety of environments, and to routing and data storage generally.

With respect to medical imaging environments that implement the DICOM protocol, routing module 36 may arrange routing information 34 to map DICOM "AENames" to default routes within system 2. Furthermore, routing information 34 may define a number of communication ports of the router, and within each port a set of acceptable AENames. This configuration can be particularly useful in enforcing security between medical imaging devices within the system 2. In addition, router 10 may support a number of unique Internet Protocol (IP) addresses. For each IP address, therefore, routing information 34 may define a number of ports, and a number of corresponding AENames. In this manner, routing module 36 arranges routing information 34 to provide access to the available AEs within one or more DICOM domains, thereby allowing router 10 to present a multiple AE interface to a DICOM domain with which medical imaging devices of system 2 can readily communicate.

Consequently, the AEName mapping supported by router 10 facilitates "collaborative" archiving in which requests are automatically forwarded to a number of appropriate destinations. In particular, router 10 maps an AEName and a type of request to a list of destinations within system 2. In one embodiment, routing information 34 includes two database tables to map a "called" AEName to a list of destinations. More specifically, routing module 36 maintains a "Basic Connection Information" table within routing information 34 to identify other devices within system 2 that need to receive a copy of an inbound asset. In one embodiment, the Basic Connection Information table contains the following Information:

Called AE Name—A name used to uniquely target (restrict) access to specific destinations.
Request Type—Designates the type of request—i.e. "Store, Query, or Move"
    Type=Store (Transfer information to Archive(s))
        List of routers to receive data on store requests from this request name. This may be a list of 1-n Router Names.
    Type=Query (Transfer Query to Archive(s))
        List of 1 to N routers to receive request information for a query request from this request name.
    Type=Move (Transfer "Move Request" to Archive)
        Router to request specific archive to retrieve data.
HostName/IP address—Address used to form a connection to this Router. A zero in this field indicates that this router is a "Destination" for this data.
Port Number—Port number used for connection to this router
Encryption—Enumerated field with the type of encryption to be used on the connection. (i.e. Public/Private key encryption.)
Compression—Enumerated field with the type of compression to be used in this connection.

In addition, a "Local Destination" table within routing information 34 stores the data necessary for router 10 to form connections with the other devices in the network. In one embodiment, the Local Destination table contains the following information:

Called AE Name—Name used to uniquely target (restrict) access to specific destinations.
New Called AE Name (Used by the Storage SCU agent as the "Calling AE Name".)
Instance UID (To specifically identify an instance of an application running on the target SCP system.)
HostName/IP address—Name/Address of the DICOM System to receive the data. (A 0 in this field indicates that the data is destined for an archive that is locally defined.
Port Number—Port number used to connect to the Locally (LAN) attached DICOM Device.

Router 10 may also maintain a set of rules 38 to further control routing of inbound network communications 32. Routing module 36 may use rules 38 to redirect a network communication to a different route, to evoke an additional action, such as deleting the data or reconciling the data, or to send the network communication to one or more additional destinations.

Consequently, router 10 may implement a two-tier routing system in which routing module 36 first examines destination information within an inbound network communication 32, and then applies rules 38 to the incoming data to determine the ultimate route(s). In this manner, routing module 24 may inspect at least a portion of the encapsulated non-pixel data before forwarding the asset to one or more destinations. Rules 38 may also be used to map or correct tagged data prior to routing. Router 10 may parse the incoming data, and use rules 38 to map a tag to a new meaning or format. A rule may be created, for example, to automatically reformat patient identifiers as received from a medical imaging modality. Furthermore, the rules may be used to selectively propagate or filter messages or particular commands, such as DICOM commands, along one or more specific routes.

In one embodiment, routing information 34 describes each route as either "local" or "external." External routes may be further qualified as "direct" or "batch." A local route descriptor causes routing module 36 to route an inbound asset to local database 40. Conversely, an external route descriptor causes routing module 36 to route an asset to a networked device within system 2. Furthermore, a "direct" external route descriptor causes router 10 to immediately forward the asset to the destination. Router 10 waits until receiving an acknowledgement from the destination before sending an acknowledgement back to the source modality. In this manner, the asset is stored in multiple locations, and router 10 guarantees storage of the asset to the modality with a single acknowledgement. A "batch" descriptor for an external route, however, causes router 10 to store the asset locally and immediately acknowledges the source modality. At a later point in time, router 10 batch transfers the buffered assets to their respective destinations. This mode may advantageously increase patient throughput at the modalities.

Connection manager 42 receives storage asset of inbound network communication 32, typically from a medical modalities upon completion of an exam, and initiates the routing process of router 10. In particular, connection manager 42 listens to a well-known communication port for communications from any network device. Upon receiving a message from such a device, connection manager 42 immediately invokes two software modules, such as by instantiating two threads, for parallel processing the inbound storage asset. Connection manager 42 instantiates storage manager 44, which is responsible for receiving and buffering an incoming asset to local storage 49, and verification module 46, responsible for validating the non-pixel data encapsulated within the storage asset.

After invoking storage manager 44 and verification module 46, connection manager 42 directs the inbound communications to a new socket, and passes a handle to the socket to each of storage manager 44 and verification module 46. In this manner, storage manager 44 and verification module 46 receive data of an inbound asset in parallel, each processing selected portions of the asset. Consequently, router 10 may be able to achieve higher utilization of network bandwidth by ensuring that assets are quickly and efficiently retrieved from network 14. This is particularly advantageous in the medical imaging environment where the data portions can be significantly large. In one embodiment, storage manager 44 and verification module 46 make use of a ringtail buffer that stores data of the inbound asset as router 10 receives the from the network. The use of a single buffer allows verification module 46 and storage manager 44 to avoid multiple copies of the asset, which saves processing time, memory space, and can reduce errors and discrepancies.

Storage manager 44 receives the asset, including tagged data and pixel data, and stores the asset to local storage 49 at a high rate. In one embodiment, storage manager 44 streams the incoming asset to a file located on a high-speed computer readable medium within the router, such as a hard disk.

Verification module 46 receives and process the non-pixel data within the asset to verify and validate all syntactical and semantical information. Within a medical imaging environment, for example, verification module may verify and validate all syntactical and semantical information of the encapsulated patient information, session information, study information and image information. Verification manager 46 extracts non-pixel data associated with each image, and stores the non-pixel data in temporal database 40A, permanent database 40B, or both, thereby allowing an operator to retrieve the information during a subsequent examination. In one embodiment, temporal database 40A is configured to automatically prune assets after a period of time.

Upon detecting missing or invalid data within an incoming asset, verification module 46 issues a reconciliation event 37 to patient manager 48, which provides for the reconciliation of medical imaging data, such as patient information, session information and the like. In one mode of operation, router 10 does not forward storage assets to destinations, such as central storage system 12, until the encapsulated data has been fully reconciled.

In one embodiment, verification module 46 maintains a DICOM dictionary within local database 40 for storing "private" (user-defined) DICOM tags that are defined by modalities and other devices within the system. When verification module 46 encounters a new private tag, verification module 46 collects and stores all pertinent information related to the private tag including, for example, a UID, a version, and a source for the tag. In this manner, router 10 builds the DICOM data dictionary in "real-time." Based on this information, router 10 can uniquely identify where the private tags originate.

Upon validation of the encapsulated data by verification module 46, routing module 36 examines non-pixel medical image data from message queues 41, determines the appropriate route, and enqueues a network communication within output queues 48 for transmission to a destination by output interface 47. The queued outbound network communication contains pointers to corresponding non-pixel data within message queues 41 and portions of the pixel data stored on local storage 49. In this manner, routing module 36 may ready a storage asset for output communication, even prior to storage manager 44 writing the entire pixel data of the asset to the local storage 49. Consequently, router 10 may commence an outbound network communication 45 of an asset prior to receiving all of the asset data from inbound network communication 32. While outputting the communication to the network, output interface 47 uses the pointers to read the messages from message queues 41 and extracts the corresponding pixel data from the local storage 49 to form an outbound communication.

Furthermore, routing module 36 and output interface 47 are capable of sending storage assets to multiple destinations in parallel such that the assets are available when needed by medical professionals. If a particular doctor works in two hospitals and a clinic, for example, routing module 36 may route the assets generated from an examination to multiple devices at both hospitals and the clinic. Output interface 47 communicates the assets to the multiple destinations in parallel.

As discussed above, verification module 46 issues a reconciliation event 37 when encapsulated data of an inbound network communication 32 is invalid or missing. Upon receiving a reconciliation event 37, patient manager 48 examines routing information 34 to identify network destinations that may store relevant patient information, and queries the remote destinations in an attempt to automatically reconcile the data. Patient manager 48 may, for example, invoke HIS/RIS interface 39 to retrieve patient data from a remote HIS/RIS system 8. In this manner, patient manager 48 may leverage routing information 34 to identify the available data sources within the system 2. In addition, as illustrated below, patient manager 48 provides a user interface by which an operator can manually query the remote network resources and reconcile the non-pixel data within a storage asset, such as the demographical information for a patient.

Patient manager 48 performs a number of quality control functions in addition to reconciling data, including asset reprocessing, patient management, and pre-fetching assets prior to an examination of a patient. In general, the patient management functionality allows an operator to update patient information, delete a patient, or otherwise manage patient data stored within the local database or a master database. In addition, patient manager 48 facilitates system wide searching by leveraging routing information 34. By interacting with a user interface presented by patient manager 48, an operator can search local database 40 for images, or direct patient manager 48 to send search requests to other medical devices in accordance with routing information 34.

Figure 4:
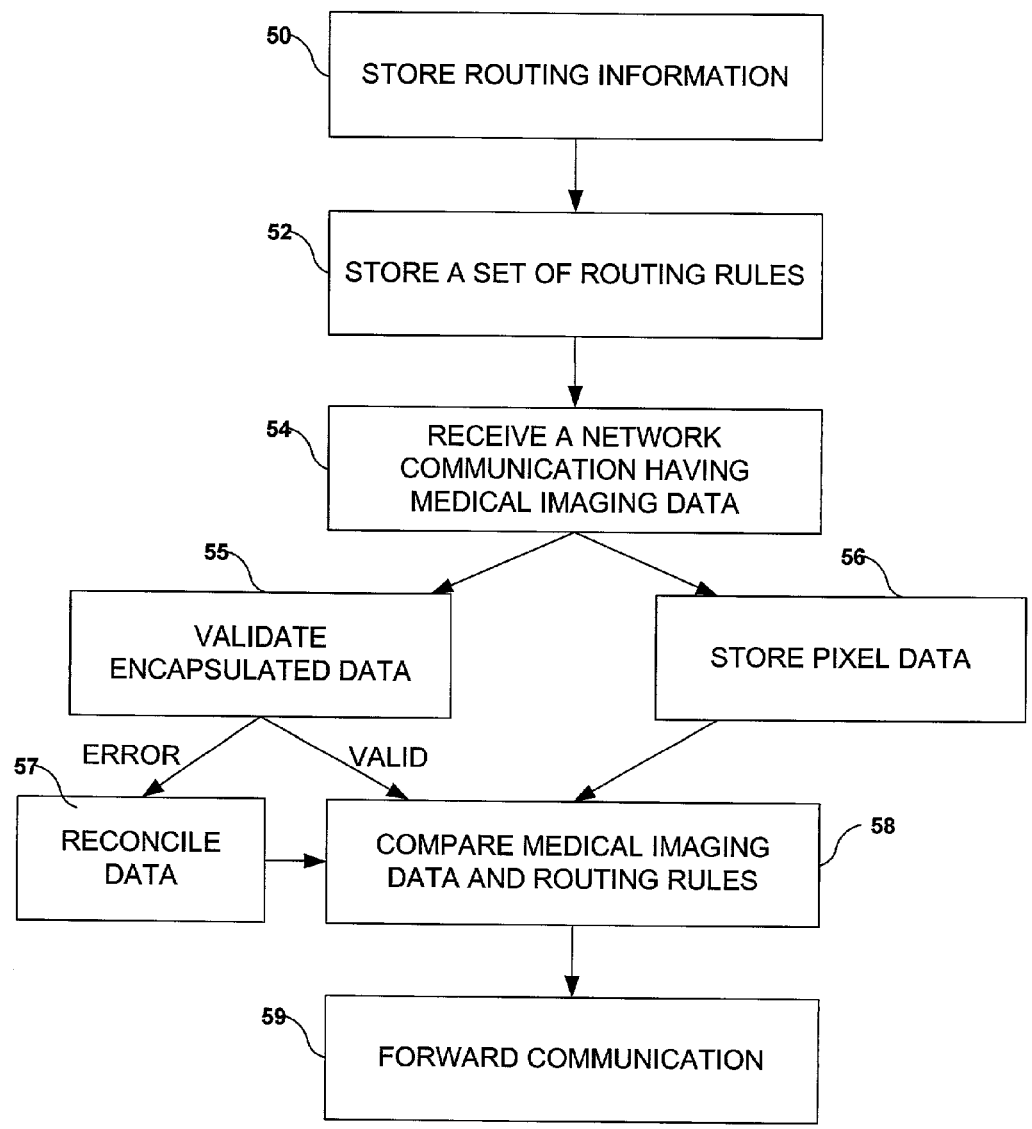
FIG. 4 is a flowchart providing a high-level overview of the routing process.

FIG. 4 is a flowchart providing a high-level overview of the routing process carried out by router 10. As described above, router 10 stores routing information 34 that describes routes between the networked medical imaging devices within system 2 (50), and stores a set of rules 38 to further control routing of network communications (52).

Upon receiving a network communication comprising one or more medical imaging assets (54), router 10 validates the encapsulated non-pixel medical imaging data (55) and buffers the pixel data to a local storage (56) in parallel. Upon validating the data, or upon reconciling and invalid or missing data (57), router 10 identifies destination information within the assets, and compares the non-pixel medical imaging data encapsulated within the assets to the set of rules 38 (58). Router 10 forwards the network communications in accordance with the destination information and the results of the comparisons (59).

Figure 5:
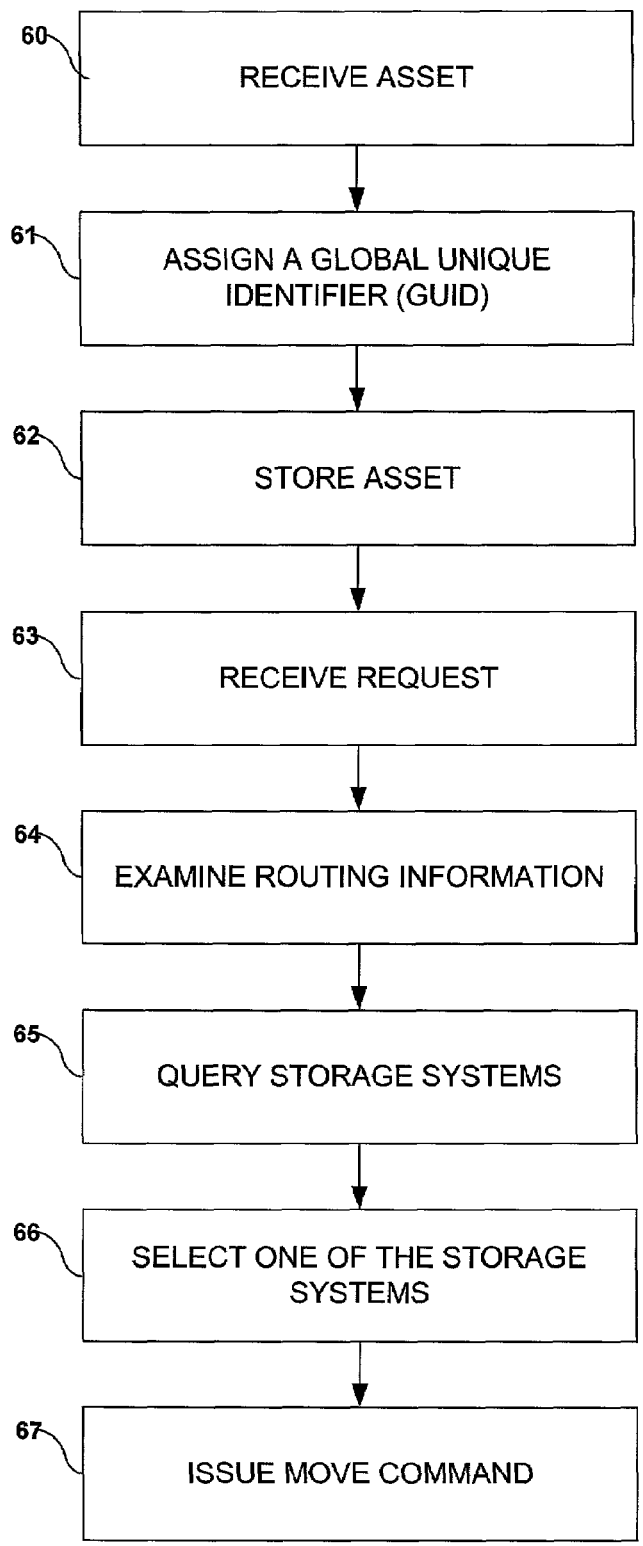
FIG. 5 is a flowchart illustrating the integration of routing and storage functionality to manage medical imaging assets within a medical imaging system.

FIG. 5 is a flowchart illustrating the integration of routing and storage functionality to manage medical imaging assets within a medical imaging system. Upon receiving a new asset from a source modality (60), such as upon completion of an examination of a patient, router 10 queries central storage system 12 for a new global unique identifier (GUID) (61). Upon receiving the new GUID for the asset, router 10 forwards the asset to one ore more storage devices, such as a local archive 20 and central storage system 12 (62). In this manner, system 2 maintains unique global identifiers for each copy of a storage asset. This technique has many advantages, including simplifying routing assets between multiple storage systems and medical imaging devices.

An operator, such as a physician, may periodically wish to view stored assets. Upon receiving a subsequent request for the stored asset (63), router 10 examines routing information 34 to identify storage systems within system 2 (64). In other words, router 10 leverages routing information 34 to facilitate identification of potential locations within system 2 for a requested asset. Upon identifying the locations, router 20 queries the storage system to locate the requested asset (65). Router 10 may, for example, issue one or more "CFIND" commands to the storage systems to determine which storage systems are currently storing the requested asset, or copies thereof.

Because multiple copies of the asset may exist within system 2, one or more of the storage systems may respond to queries. Router 10 selects one of the storage systems based on a variety of criteria (66), including bandwidth of network connections between the storage systems and the requesting device, speed and type of media used by the storage system, and whether the requested asset is immediately accessible by the storage systems, or must be retrieved from an offline storage medium, such as tape. Upon selecting one of the storage systems, router 10 issues a move command to the selected storage system to move the requested asset to the requesting medical imaging device (67).

Figure 6:
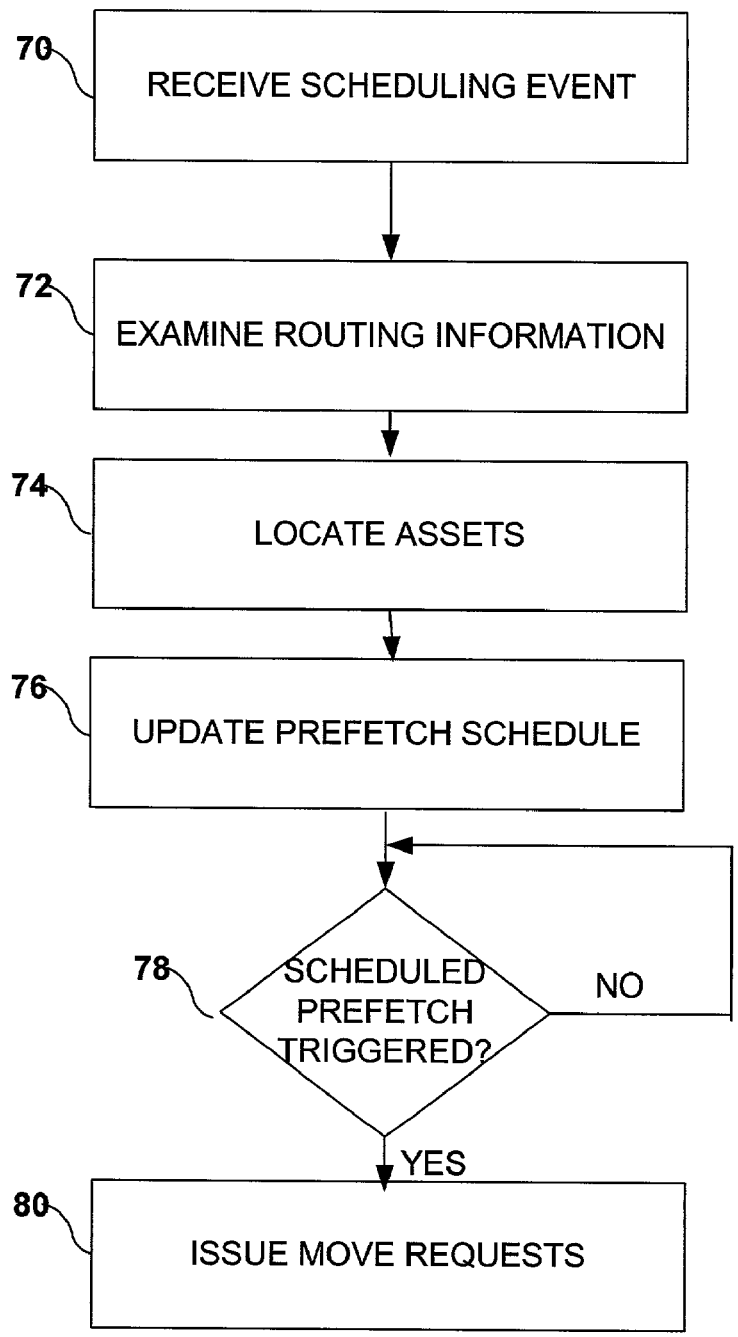
FIG. 6 is a flowchart illustrating a mode of operation in which a router uses routing information to facilitate the pre-fetching of storage assets.

FIG. 6 is a flowchart illustrating a mode of operation in which router 10 uses routing information 34 to facilitate the pre-fetching of storage assets, thereby making the assets immediately available physicians and other operators. Router 10 may, for example, pre-fetch storage assets for a patient prior to a follow-up examination of the patient.

Typically, an operator will interact with the HIS/RIS system 8 and schedule an examination of a patient. In response, HIS/RIS system 8 will issue a scheduling event (70) through a standard communication protocol such as HL7. Upon receiving the event, router 10 examines routing information 34 (72) to identify available routes within system 2, and issues queries, such as CFIND commands according to the DICOM protocol, to locate the assets related to a particular patient (74).

After locating the assets, router 10 updates a pre-fetch schedule based on the locations of the assets, the scheduled time for the examination, and characteristics of the links within system 2 including availability and cost (76). In particular, router 10 may present a user interface by which an operator can identify and select the particular patient information to be pre-fetched prior to the examination. By interacting with the interface, the user can view patient information and schedule pre-fetching the corresponding assets.

At the scheduled time (78), router 10 initiates the cooperative pre-fetching and movement of the assets by issuing 1 to N move commands to move the assets from storage devices to the modality scheduled to perform the patient examination and imaging session (80). Typically, a batch move software module operating on router 10 examines the pre-fetch schedule, and moves the assets as needed to an appropriate temporal storage within one or more departments 6. In particular, router 10 selects the relevant assets to move in accordance with rule set 25. Router 10 may, for example, move a subset of the located assets based on the modality type, patient ID, examination area of a patient, and the like. In this manner, router 10 may not necessarily move all of the assets for a given patient, but only those assets relevant to the scheduled examination.

Router 10 performs similar operations upon receiving a CFIND request from another medical imaging device within system 10, such as another router. In response to receiving a CFIND request, for example, from another router, router 10 examines routing information 34 to map the designated AEName to a route, and then to one or more locations. Router 10 then issues CFIND requests to the identified locations in accordance with routing information 34 in order to locate all of the assets associated with a particular find request. During prefetching operations, router 10 enforces security and other policies to provide secure access to patient data.

Figure 7:
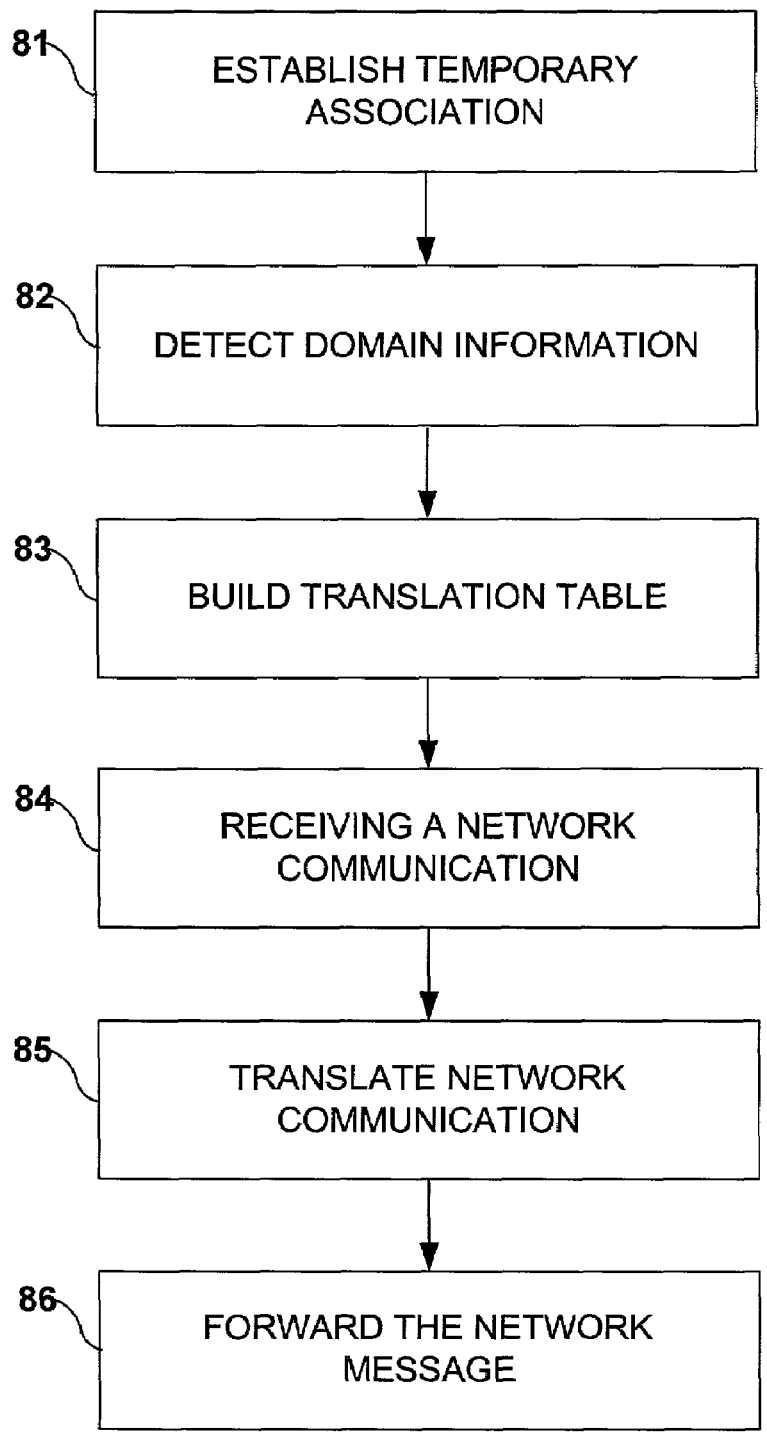
FIG. 7 is a flowchart illustrating the integration of multiple medical imaging departments.

FIG. 7 is a flowchart illustrating the integration of multiple departments 6 via router 10 in further detail. As described above, each department 6 may include a number of different types of devices including an archive manager, a clinical view station, and a number of imaging modalities. According to the DICOM protocol, proper communication with each of these devices requires a remote device to have knowledge of, and correctly use, a number of unique identifiers specific to the DICOM "domain" of each department. A DICOM compliant device may be identified by, for example, a unique identifier, a version, and an AETitle. In order to facilitate communications with a variety of network devices, router 10 can operate in an emulation mode in which router 10 detects the identifiers, and translates inbound and outbound network communications to the department in accordance with the identifiers.

In particular, router 10 may establish a temporary connection, referred to as an "association" by the DICOM protocol, with one or more of the devices of the department (81), typically causing one of the devices to respond with a unique identifier (UID), a version number, an AETitle. Router 10 extracts the domain identifiers from the response (82) and builds a translation table for translating inbound and outbound communications from the department 6 (83).

Upon receiving an inbound or output network communication (84), router 10 parses the network communication and translates the encapsulated domain identifiers in accordance with the translation table (85). Upon translating the identifiers, router 10 forwards the network communication based on routing information 34 (86). In this manner, router 10 presents dual interfaces that map external identifiers to the assumed domain identifiers of a department or other medical imaging domain and, thereby, allows external devices to seamlessly communicate with the devices within the assumed domain. In other words, remote medical imaging devices need not know the specific domain identifiers of medical imaging devices within a department in order to communicate with the devices.

Figure 8:
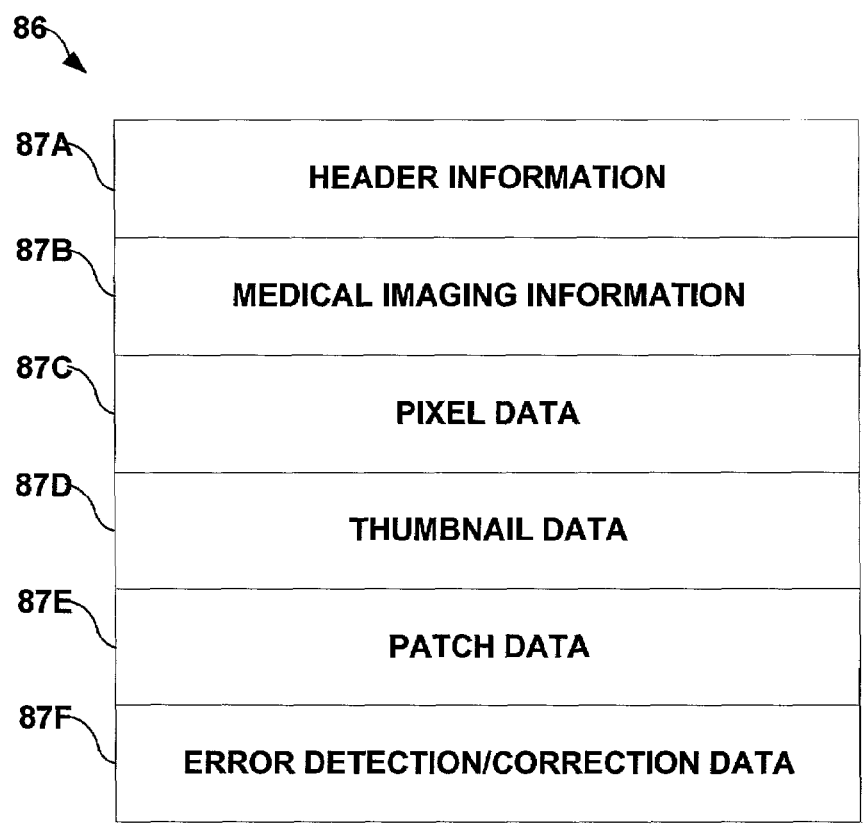
FIG. 8 illustrates a unique communication format for exchanging and interchanging data.

FIG. 8 illustrates a unique communication format 86 supported by router 10 for exchanging and interchanging data. In the illustrated embodiment, format 86 includes asset meta information 87A, medical imaging information 87B, pixel data 87C, thumbnail data 87D, patch data 87E, and error correction and detection information 87F Header information 87A includes all routing information necessary for router 10 to route the asset within system 2. Medical imaging information 87B includes raw data received from the modality that describes the recent examination, including the patient information, session information, study information and image information. Medical imaging information 87B may include, for example, related DICOM tags and messages. Pixel data 87C includes the medical images generated by the examination, while thumbnail data 87D includes low-resolution versions of the images for quick display. Thumbnail data 87D contains data that router 10 has extracted from the pixel data 87C, and stored for quick access by view stations. This allows for the "pre-building" and retention of thumbnail data so that the data can be quickly retrieved and displayed.

Patch data 87E includes all modifications to medical imaging information 87B, which was originally generated by the source modality. In other words, the original data is not modified. Rather, the asset includes patch data 87E that stores all of the updated data and, in particular, a revision history including the date and time of the change, and operator that made the change. In other words, during the reconciliation process, patient manager 48 stores all updates and modifications of an asset within the patch data 87E of the exchange format 86. In this manner, exchange format 86 facilitates compliance with regulations that require change tracking and revision histories and furthermore, facilitates storages of the information within a single self-describing data asset.

When a view station presents the data to an operator, patch data 87E overrides the medical imaging 87B. However, the operator may always view the revision history and the original medical imaging data 87B. Error detection and correction information 87F, such as a cyclical redundancy check (CRC), includes additional data useful for detecting changes to data encapsulated by an asset, or errors during transmission. The following description provides further details an example file format 86 for use with DICOM storage assets.

For use in a DICOM compliant environment, the contents of the header information 87A is defined to document ownership and version control, and to provide a mechanism to gain efficient access to other parts of the format. The contents may be as follows:

Version [25]—Documents the version of this File. "Format V1.00"

CopyRight [120]—Legal Statement identifying the ownership of this format.

StartOfHeader—Offset from beginning of file to start of Header (Normally 0)

EndOfHeader—Offset from beginning of file to End of Header

StartOfCommand—Offset from beginning of file to Start of DICOM Command Data

EndOfCommand—Offset from beginning of file to End of DICOM Command Data

StartOfData—Offset from beginning of file to Start of DICOM Data

EndOfData—Offset from beginning of file to End of DICOM Data

StartOfPixel—Offset from beginning of file to Start of Pixel Data

EndOfPixel—Offset from beginning of file to End of Pixel Data

StartOfThumbnail—Offset from beginning of file to Start of Thumbnail Data

EndOfThumbnail—Offset v End of Thumbnail Data

StartOfPatches—Offset from beginning of file to Start of Patch Data

EndOfPatches—Offset from beginning of file to End of Patch Data

DestinationAPTitle [DILIB_VR_LENGTH_AE+1]—Called AE Name in DICOM Association (Target for Storage of this Image)

ImageGUID [DILIB_GUIDLENGTH]—Image GUID within ADA Database

SeriesGUID [DILIB_GUIDLENGTH]Series Folder GUID within ADA Database

StudyGUID [DILIB_GUIDLENGTH]—Study Folder GUID within ADA Database

PatientGUID [DILIB_GUIDLENGTH]—Patient Folder GUID within ADA Database

ADASeriesToStudyGUID [DILIB_GUIDLENGTH]—Series to Study GUID within ADA Database ADAStudyToPatientGUID [DILIB_GUIDLENGTH]—Study to patient GUID (Link) within ADA Database Checksum—Checksum computed when data arrives at an archive Port—Port number used when data was transmitted TransferSyntax—Transfer Syntax used to transfer this data ApplicationContextName [DILIB_VR_LENGTH_PN+1]—Application Name (If Present) of device that stored this data to an archive.

CallingAPTitle [DILIB_VR_LENGTH_AE+1]—Calling AE Name used by calling device to create association CalledAPTitle [DILIB_VR_LENGTH_AE+1]—Called AE Name used by calling device to create association RespondingAPTitle [DILIB_VR_LENGTH_AE+1]—Responding AE Name when Association was internally generated.

MaxPDU—Max PDU Size as negotiated on the Association.

Result—DUL Result captured when Image Arrived

ResultSource—DUL ResultSource captured when Image Arrived

Diagnostic—DUL Diagnostic Value captured when Image Arrived

CallingPresentationAddress [DILIB_VR_LENGTH_UI+1]—Calling HostName/IP address for association CalledPresentationAddress [DILIB_VR_LENGTH_UI+1] Called HostName/IP address for association MaximumOperationsInvoked—Maximum Operations Invoked from association information MaximumOperationsPerformed—Maximum Operations Performed from association information CallingImplementationClassUID [DICOM_UI_LENGTH+1]—Implementation Class UID of Calling Software—captured during Association Negotiation CallingImplementationVersionName [DILIB_MAXIMP-NAMELENGTH+1]—Implementation Name of Calling Software—captured during Association Negotiation CalledImplementationClassUID [DICOM_UI_LENGTH+1]—Implementation Class UID of Called Software—captured during Association Negotiation CalledImplementationVersionName [DILIB_VR_LENGTH_SH+1]—Implementation Name of Called Software—captured during Association Negotiation PeerMaxPDU—Max PDU for transmission to Peer Device—captured during Association Negotiation EsopLength—Extended SOP Length—captured during Association Negotiation Medical imaging information 87B contains tags defined within the DICOM as "Group 0" tags. These tags are part of Command Request/Response information that must be present with each DICOM Message. Medical imaging information 87B may also contain DICOM data tags that defined within the DICOM Standard from Group 0002, Element 0000 through Group 7FE0 Element 0000. These tags are considered the "payload" of a DICOM compliant message and contain a wide range of information relating to the patient, physician, image characteristics, and the like. These tags may be saved within the a file and arranged as follows:

<tag (group/element)><Length><Data>
<tag (group/element)><Length><Data>
<tag (group/element)><Length><Data>
.
.
.
<tag (group/element)><Length><Data>

Pixel data 87C contains the DICOM data tag group 7FE0 Element 0010 that designates the pixel data of the DICOM image(s). This tag and the corresponding pixel data are stored within pixel data 87C, which may be a "byte-for-byte" copy of the data as received by router 10 from an imaging modality.

Patch data 87E may be arranged as follows:

<tag (group/element)><Length><Data><Change Timestamp><Operator>
<tag (group/element)><Length><Data><Change Timestamp><Operator>
<tag (group/element)><Length><Data><Change Timestamp><Operator>
.
.
.
<tag (group/element)><Length><Data><Change Timestamp><Operator>

Figure 9:
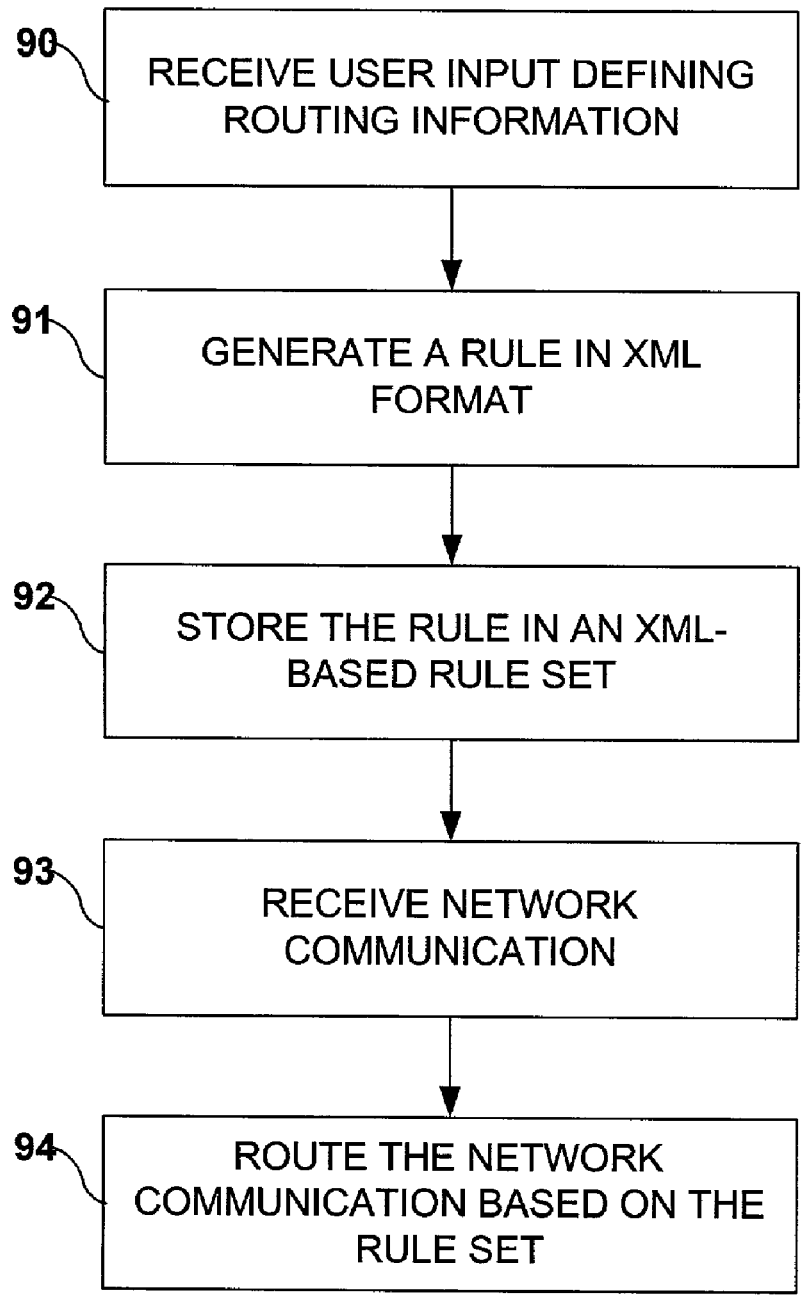
FIG. 9 is a flow chart illustrating routing of assets according to routing information and an extensible markup language (XML) based rule set.

FIG. 9 is a flow chart illustrating routing of assets according to routing information 34 and an XML-based rule set 38. As described above with reference to FIG. 3, routing module 36 implements a two-tier routing scheme in which routing module 36 first examines destination information within a network communication, such as an AEName, and then applies rules 38 to the incoming data to determine the ultimate route(s). Advantageously, routing module 24 maintains the rule set in eXtensible Markup Language format (XML) by which the user can easily create a complex grammar for routing assets. For example, the user may create rules for routing assets based on patient ID, modality, referring physician and the like. In addition, the user may define any number of tags to control routing of assets by router 10.

Initially, router 10 presents a user interface by which a user defines a set of routing rules (90). In particular, the user interacts with the user interface to define a grammar and logic for a rule for routing assets within system 2. Based on the received input, router 10 generates a rule in XML format (91) and updates rule set 24 (92).

Once router 10 has updated rule set 38, routine module 10 applies the XML-based rules to network communications. In particular, router 10 receives a network communication (93), such as an asset containing medical imaging data, assesses the rules of rule set 24 based on the network communication, and routes the network communication accordingly (94).

Figure 10:
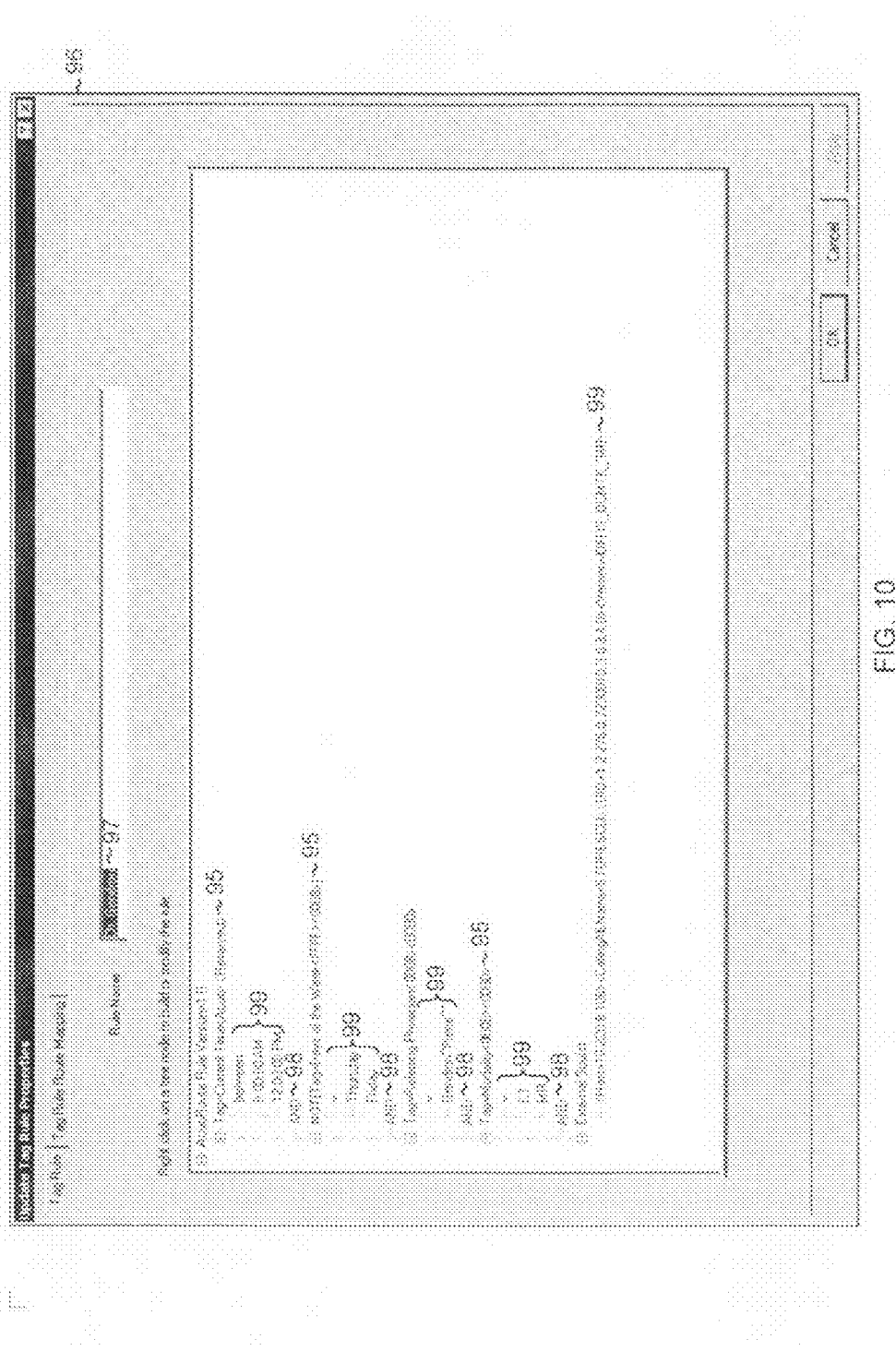
FIG. 10 illustrates an example user interface presented by a router by which an operator hierarchically defines routing logic and constructs a rule for a rule set.

FIG. 10 illustrates an example user interface 96 presented by router 10 by which an operator hierarchically defines routing logic and constructs a rule for rule set 38. In particular, the operator can input a rule name 97, and hierarchically define specific data tags, 95, logical operators 98 and corresponding data values 99 for the rule as a complex grammar.

Figure 11:
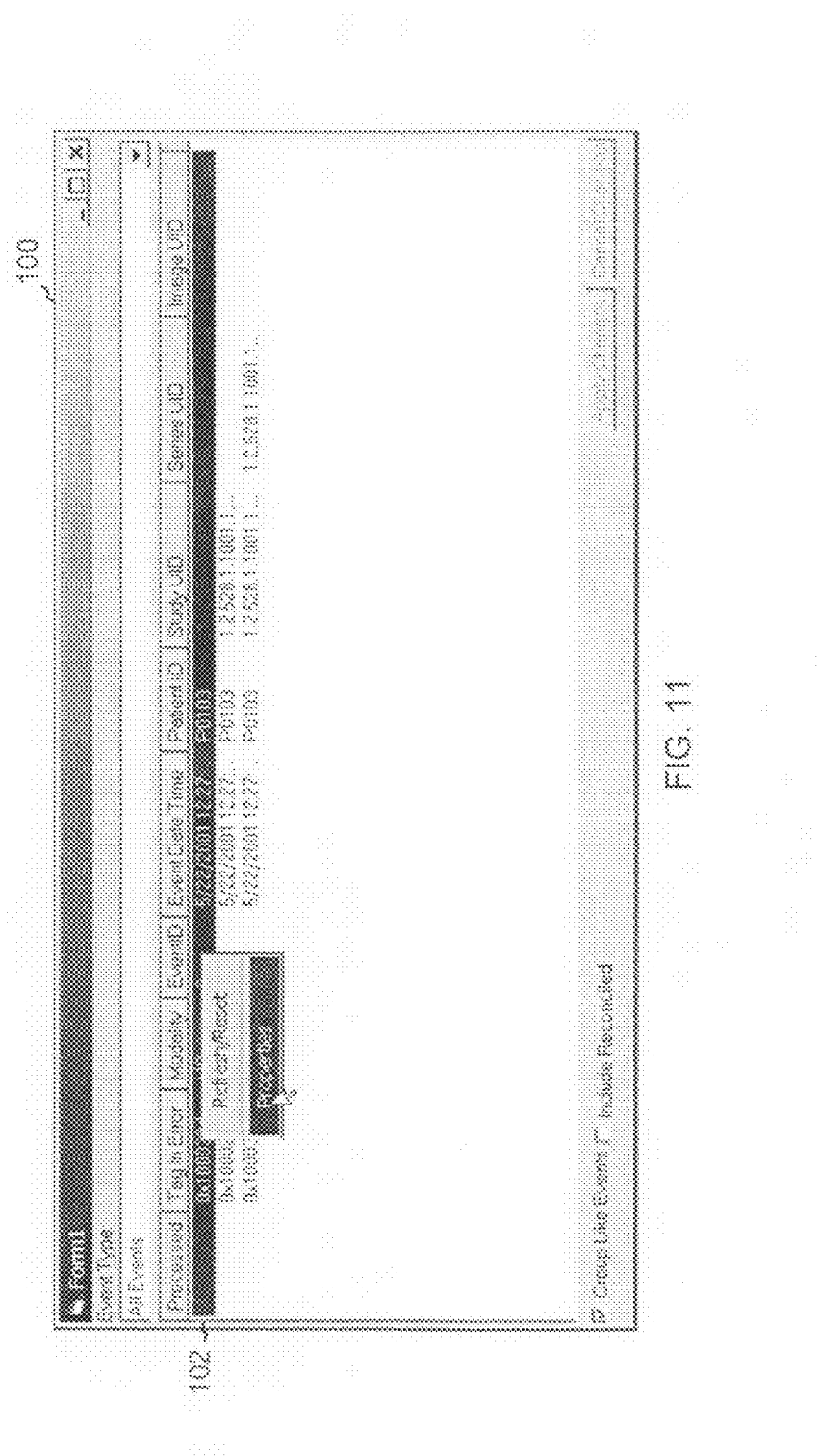

FIG. 11 illustrates an example user interface presented by patient manager 48 upon detecting errors within medical imaging data received from the various departments 6. In particular, user interface 100 displays a list of reconciliation events that have been generated by router 10 upon receiving and detecting mismatched or otherwise invalid data. In the illustrated example, interface 100 displays event list 102 having three events. For each event, interface 100 displays an identifier for the medical imaging tag corresponding to the data in error, a source medical imaging modality, an event identifier, a date and time of the event, a patient identifier, a study identifier, a series identifier, and an image identifier. For each event, the use may select and highlight the event and elect to view the properties of the event.

Figure 12:
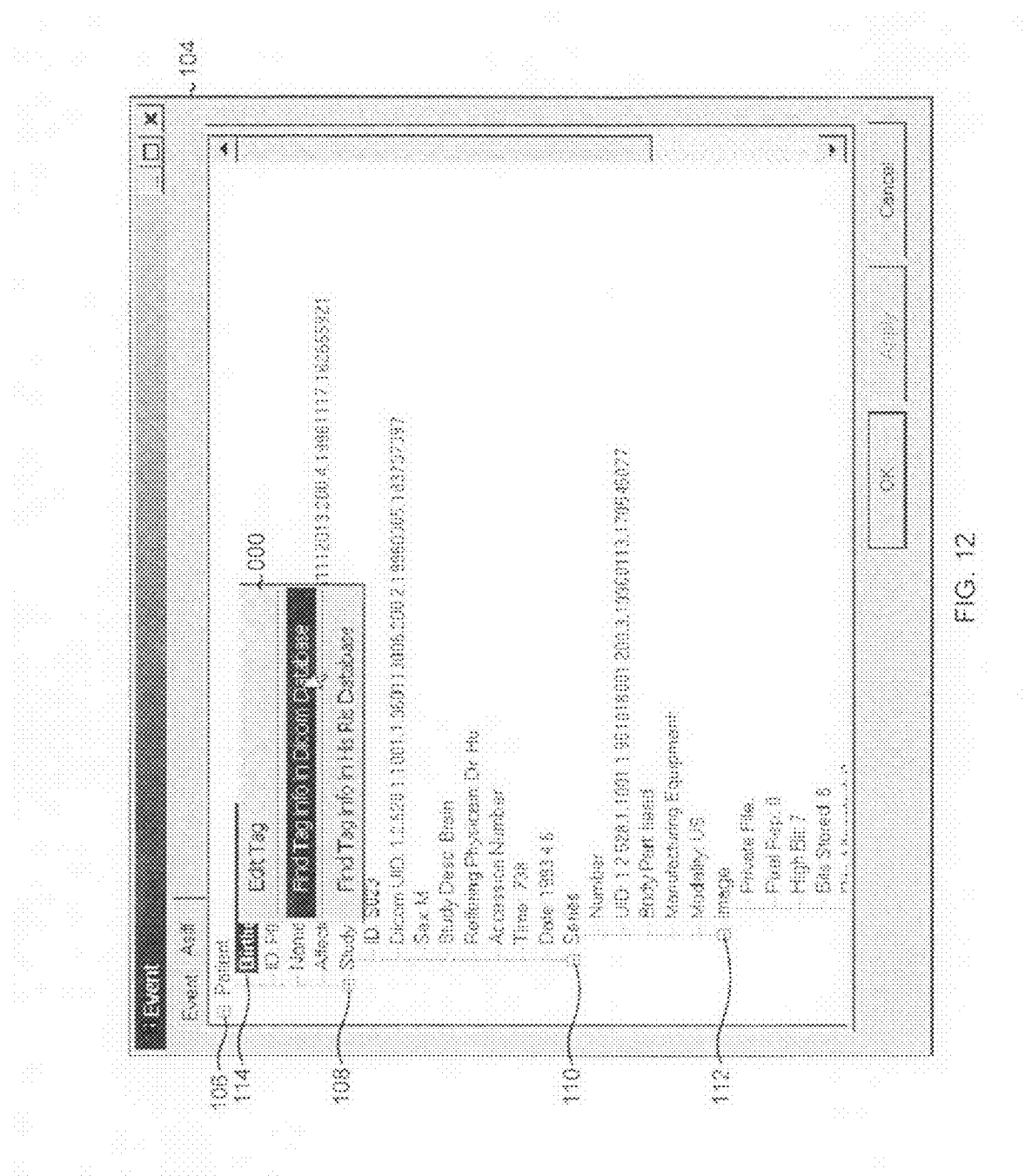

FIG. 12 illustrates an example user interface 104 displayed by patient manager 48 when the user elects to view the properties of a particular reconciliation event. In particular, user interface 104 displays the data associated with the event in hierarchical fashion. User interface 104, for example, displays patient data 106, study data 108, series data 110, and image data 112 that relate to the event. In addition, user interface 104 highlights the tag 114 for which patient manager 48 has identified missing or invalid data. Upon selecting the tag, user interface 104 displays window 116 by which the user can reconcile the data. In particular, the user may elect to edit the data directly, or search a number of resources within system 2, including a DICOM database storing medical imaging information, as well as an HIS/RIS database. Upon selecting one of the resources, patient manager 48 polls the selected resource and displays any identified relevant data in order to assist the operator in reconciling the missing data in the storage asset.

Figure 13:
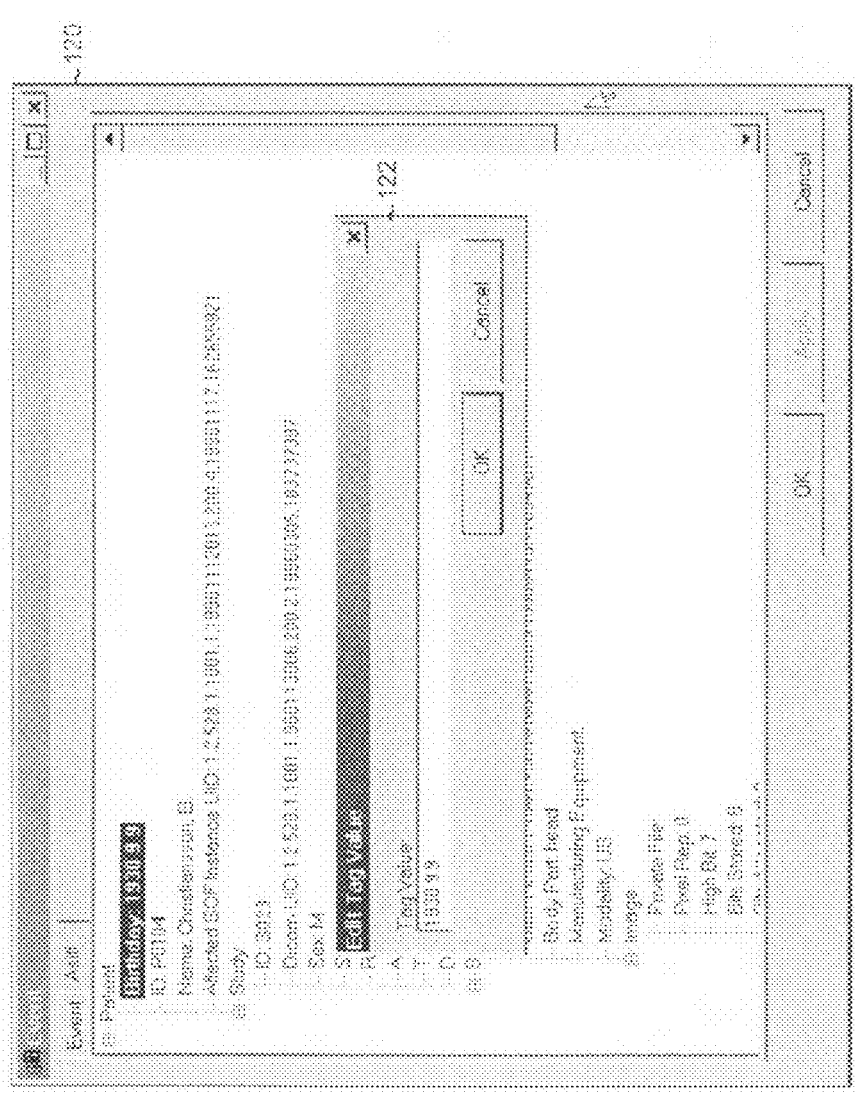

FIG. 13 illustrates an example user interface 120 displayed by patient manager 48 when the user elects to edit data element directly. During this process user interface 120 displays an edit window 122 within which the operator may enter the relevant data, thereby reconciling and clearing the event.

After receiving the data from the operator, patient manager 48 verifies that the data has been entered in the correct format.

Figure 14:
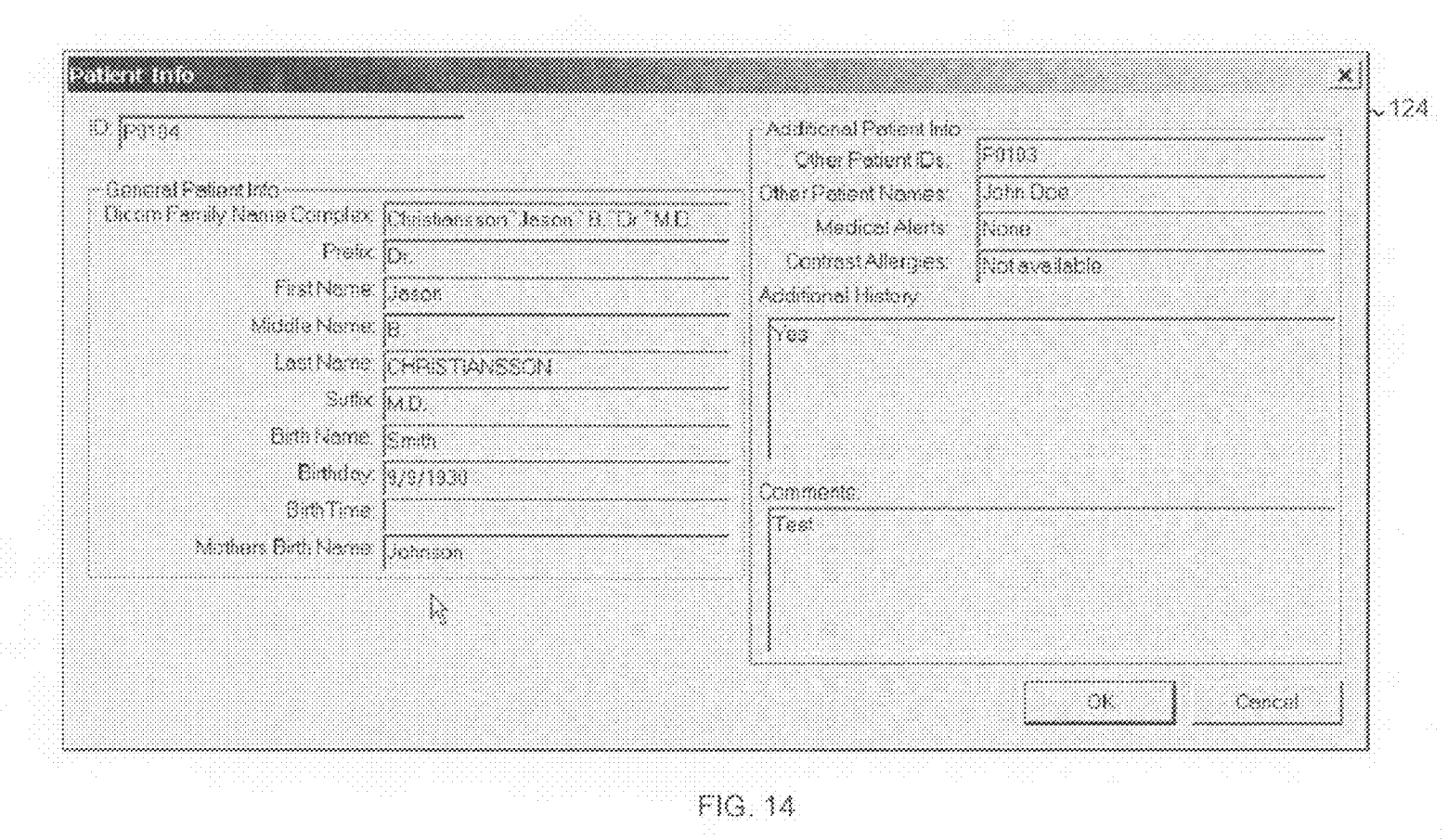
Figure 15:
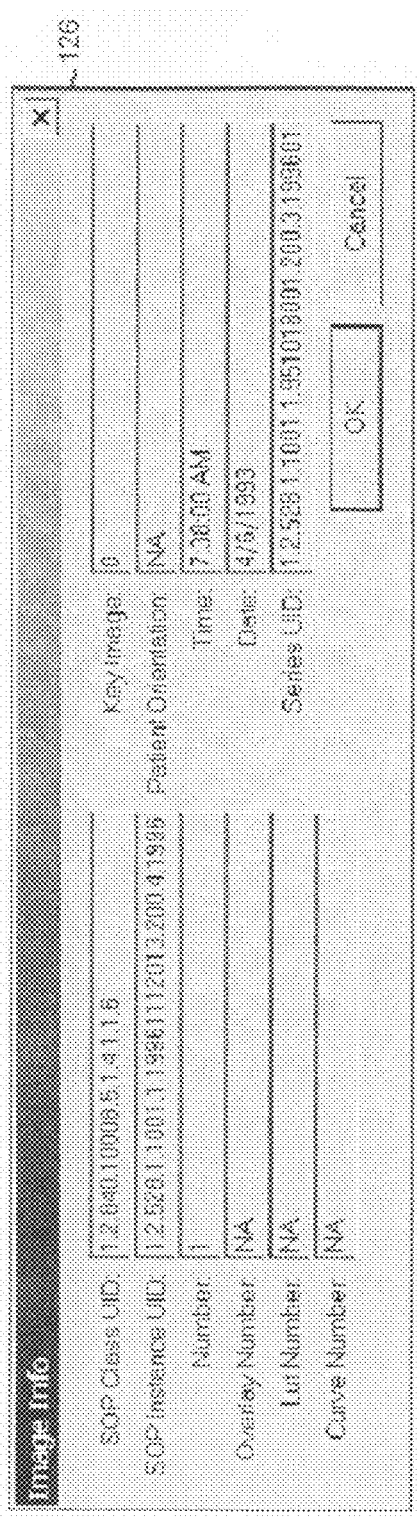
Figure 16:
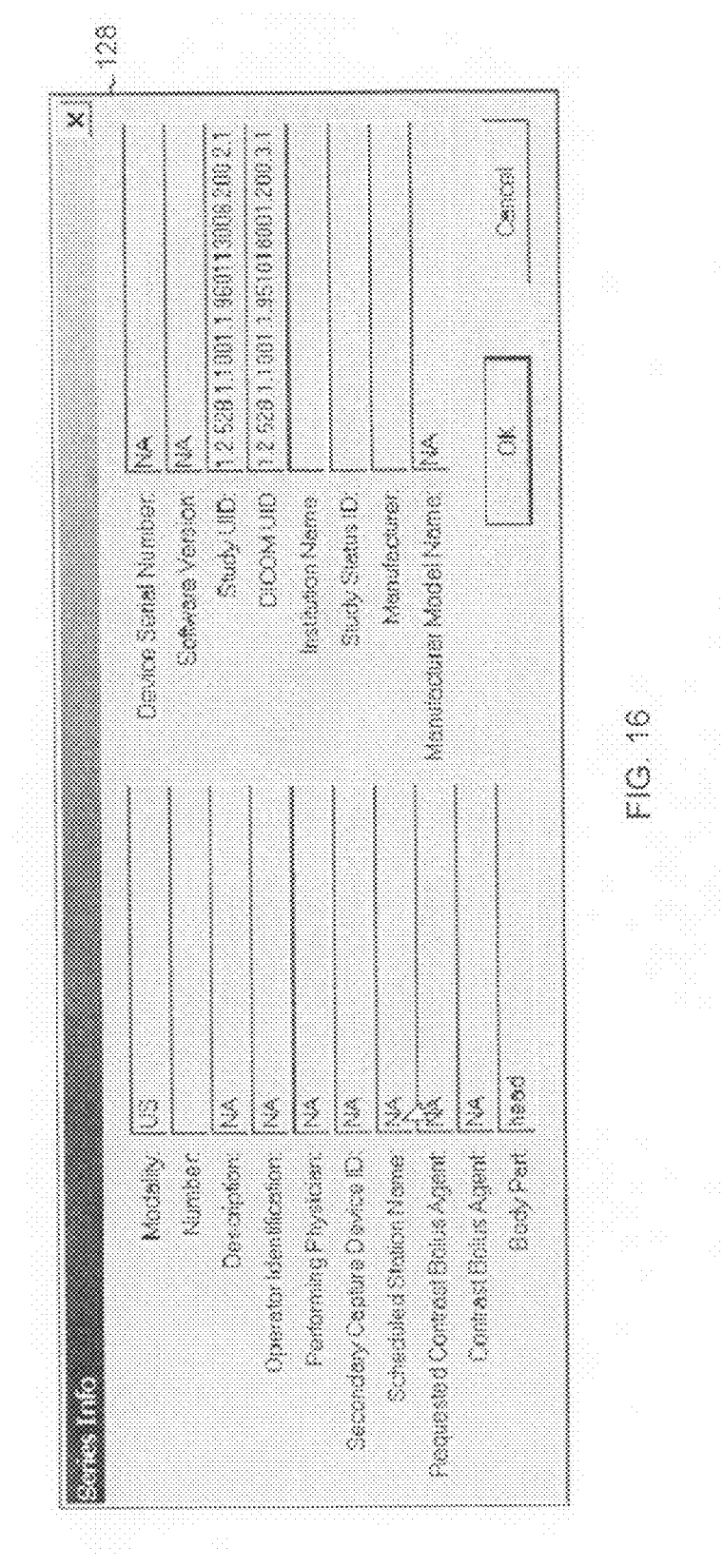
Figure 17:
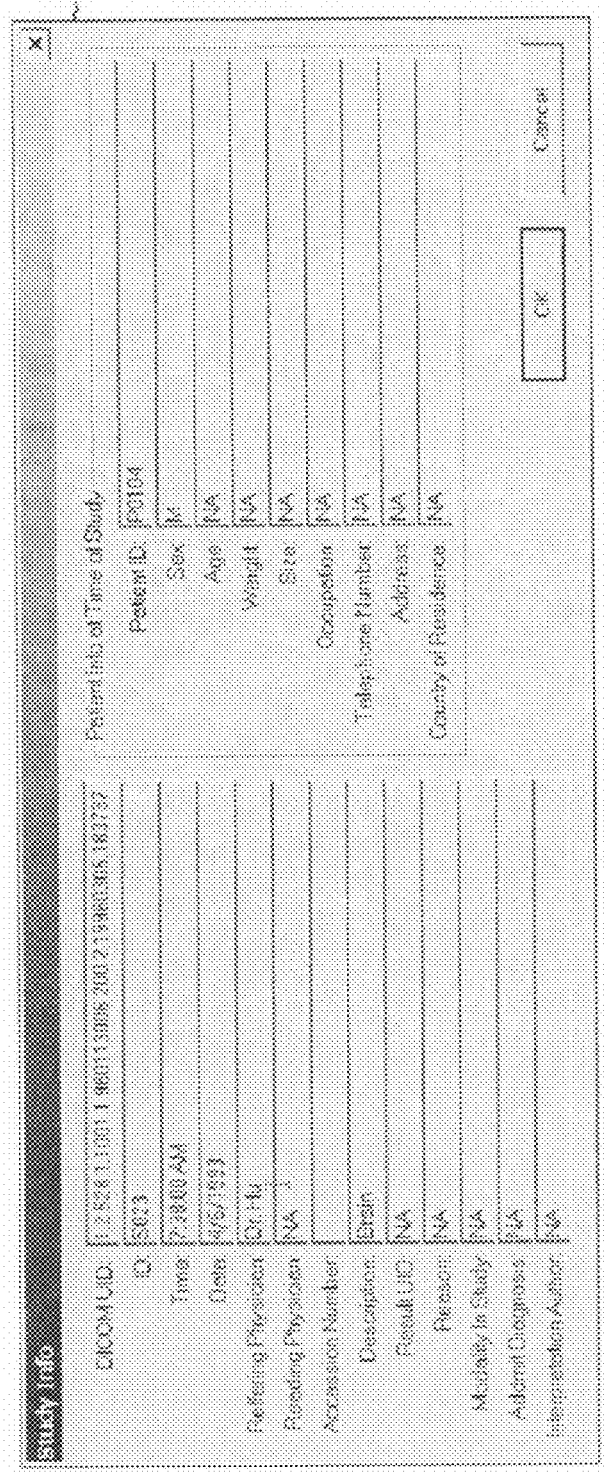

FIG. 14 illustrates an example user interface 124 displayed by patient manager 48 upon retrieving patient information from a network resource such as a DICOM database. In other words, patient manager 48 queries a network resource in order to identify and retrieve any relevant patient information that may assist the operator in reconciling the mismatched data of the current medical imaging session, and presents the information to the user. Upon viewing user interface 124, the operator may direct patient manager 48 to automatically update the missing or invalid data of the current medical imaging session. FIGS. 15, 16 and 17 illustrate similar user interfaces 126, 128, 130 displayed by patient manager 48 when the operator reconciles image information, series information and study information, respectively.

Figure 18:
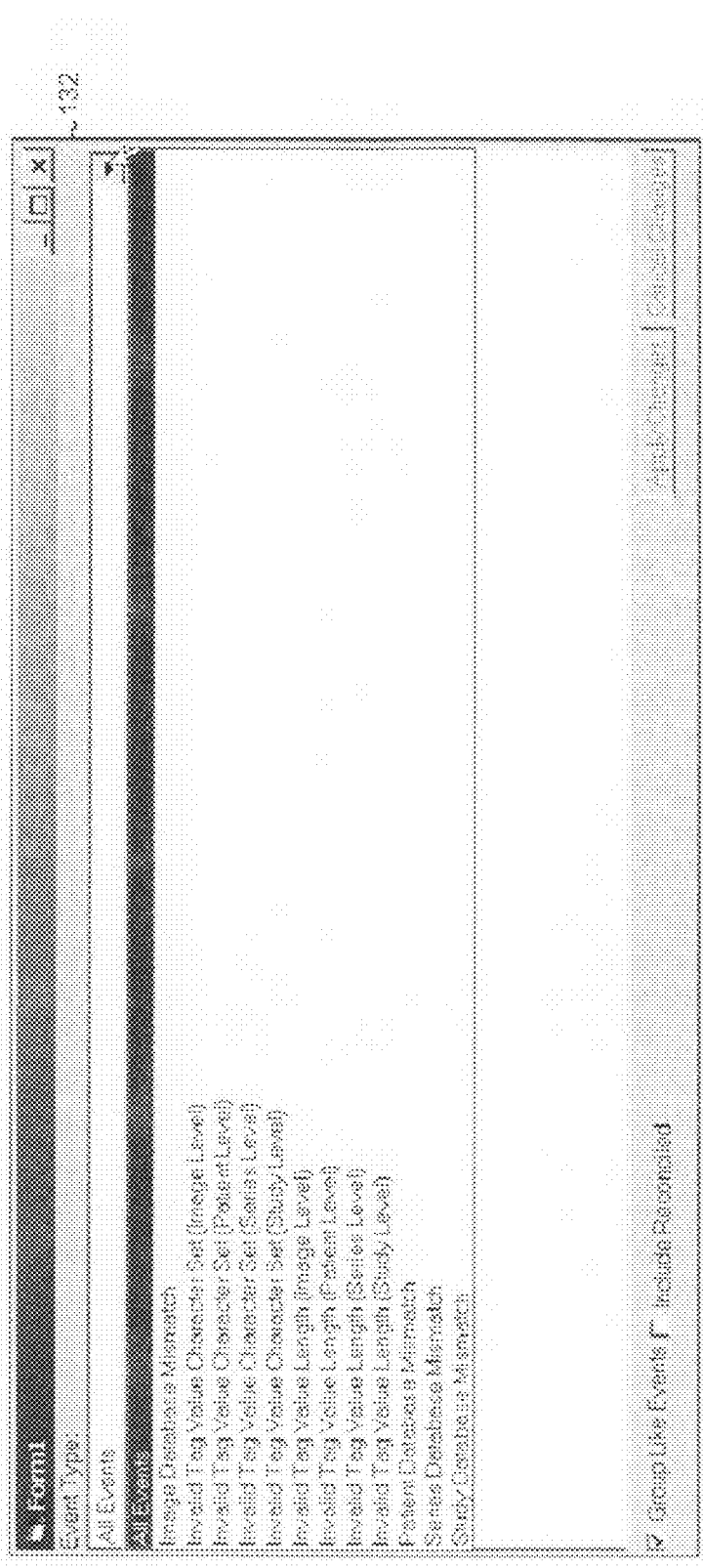
FIGS. 18-19 illustrate example user interfaces for managing patient information.

FIG. 18 illustrates an example user interface 132 displayed by patient manager 48 with which the operator interacts to batch process reconciliation events. In particular, user interface 132 allows the user to group similar events, i.e., events originating from the same imaging session in which similar data is mismatched. In this manner, the operator can reconcile common mismatched or invalid data, such as a misspelled patient name, and immediately correct and reconcile the data throughout all of the assets related to a common session.

Figure 19:
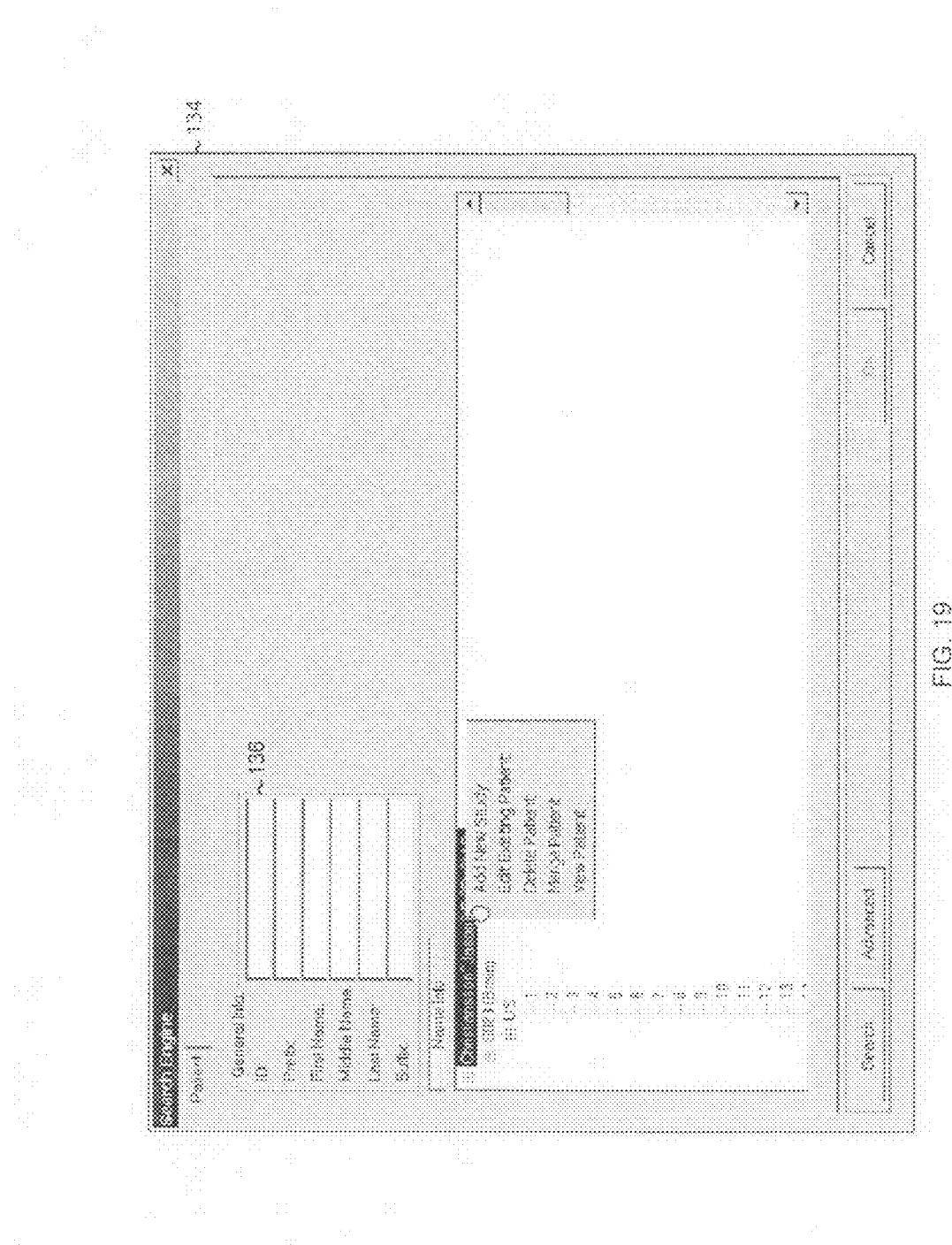

FIG. 19 illustrates an example interface 134 displayed by patient manager 48. In particular, user interface 134 provides an interface to searching functionality and patient management functionality. The operator can enter a variety of search criteria within input area 136, directing router 10 to examine the routing information, identify remote storage devices within system 2, and retrieve patient information from the storage devices or other systems such as HIS/RIS system 14. Upon retrieving relevant patient information, user interface 134 allows the operator to manipulate and otherwise maintain the patient information including initiating a new study, editing an existing patient, deleting a patient, viewing relevant patient data, and merging a number of patients into a common patient information.

Router 10 includes tracing functionality to aid in configuring, debugging and testing a medical imaging system 2. In particular, upon enabling tracing, router 10 captures binary data received in an inbound network communication and stores the data locally prior to processing and forwarding the asset. The trace output can be "piped" into debugging tools running on a local workstation or other computing device, for simulation and debugging. In this manner, a remote technical service personnel can assist in the proper configuration of router 10 within a medical imaging system 2. FIG. 20 illustrates an example display 138 presented by such a tool, including the raw hexadecimal data as well as the raw data translated into DICOM commands.

Various embodiments of the invention have been described. These and other embodiments are within the scope of the following claims.

The invention claimed is:

1. A computer-readable medium having a storage asset therein comprising:
   a first data structure that stores asset meta information to control routing of the asset through a medical imaging network;
   a second data structure that stores medical imaging information received from a medical imaging modality;
   a third data structure that stores pixel data received from the medical imaging modality;
   a fourth data structure that stores patch data that includes modifications to the medical imaging information; and a fifth data structure that stores error detection and correction information.

2. The computer-readable medium of claim 1, wherein the medical imaging information includes patient information, session information, study information and image information.

3. The computer-readable medium of claim 1, wherein the medical imaging information includes Digital Imaging and Communications in Medicine (DICOM) tags and messages.

4. The computer-readable medium of claim 1, a fourth data structure that stores thumbnail data generated from the pixel data.

5. The computer-readable medium of claim 4, wherein the thumbnail data includes a low-resolution version of the pixel data and is generated by a router within the medical imaging network.

6. The computer-readable medium of claim 1, wherein the patch data includes, for each modification, a revision history having a date, a time, and an operator associated the respective modification.

7. The computer-readable medium of claim 1, wherein the error detection and correction information comprises a cyclical redundancy check (CRC).

8. A method comprising:
storing routing information mapping destinations to routes within a network;
receiving a storage asset comprising: (i) asset meta information, (ii) original medical imaging information received from a medical imaging modality, and (iii) patch data that includes modifications to the medical imaging information;
selecting a route from the routing information based on the asset meta information; and
forwarding the storage asset according to the selected route.

9. The method of claim 8, wherein the storage asset further comprises pixel data received from the medical imaging modality.

10. The method of claim 8, wherein the storage asset further comprises error detection and correction information.

11. The method of claim 8, further comprising:
storing a set of routing rules;
comparing a portion of the medical imaging data or a portion of the patch data to the set of routing rules; and
selecting the route from the routing information based at least on a result of the comparison.

12. The method of claim 11, wherein the storage asset further comprises thumbnail data generated from the pixel data.

13. The method of claim 11, wherein the thumbnail data includes a low-resolution version of the pixel data and is generated by a router within the medical imaging network.

14. The method of claim 11, wherein the patch data includes, for each modification, a revision history having a date, a time, and an operator associated the respective modification.

15. The method of claim 8, wherein the asset meta information comprises a target Application Entity Name (AEName), and further wherein storing routing information comprises storing routing information mapping AENames to routes within the medical imaging network.

16. The method of claim 15, wherein selecting a route from the routing information comprises comparing an AEName within the storage to the AEName within the routing information.

17. The method of claim 15, further including:
updating the medical imaging information based on the patch data to form a corrected medical imaging information; and
displaying the corrected medical imaging information on a diagnostic view station.

18. A router comprising:
a computer-readable medium storing routing information mapping destinations to routes within a medical imaging network; and
a routing module to route a storage asset comprising: (i) asset meta information, (ii) original medical imaging information received from a medical imaging modality, and (iii) patch data that includes modifications to the medical imaging information, wherein the routing module selects a route based on the asset meta information and the routing information.

19. The router of claim 18, wherein the asset meta information comprises a target Application Entity Name (AEName), and further wherein the routing information maps AENames to routes within the medical imaging network.

* * * * *

UNITED STATES PATENT AND TRADEMARK OFFICE
CERTIFICATE OF CORRECTION

PATENT NO. : 7,640,171 B2
APPLICATION NO. : 09/911846
DATED : December 29, 2009
INVENTOR(S) : Gendron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2722 days.

Signed and Sealed this

Ninth Day of November, 2010

David J. Kappos
*Director of the United States Patent and Trademark Office*